United States Patent
Ko

(10) Patent No.: US 11,259,786 B2
(45) Date of Patent: Mar. 1, 2022

(54) CUTTING BIOPSY INSTRUMENT

(71) Applicant: FLOWER MEDICAL CO., LTD., Seongnam-si (KR)

(72) Inventor: Hyung Jin Ko, Anseong-si (KR)

(73) Assignee: FLOWER MEDICAL CO., LTD., Seongnam-si (KR)

( * ) Notice: Subject to any disclaimer, the term of this patent is extended or adjusted under 35 U.S.C. 154(b) by 228 days.

(21) Appl. No.: 16/481,401

(22) PCT Filed: Jan. 26, 2018

(86) PCT No.: PCT/KR2018/001177
§ 371 (c)(1),
(2) Date: Jul. 26, 2019

(87) PCT Pub. No.: WO2018/139895
PCT Pub. Date: Aug. 2, 2018

(65) Prior Publication Data
US 2019/0388072 A1  Dec. 26, 2019

(30) Foreign Application Priority Data

Jan. 26, 2017 (KR) .................. 10-2017-0012789
Jan. 26, 2018 (KR) .................. 10-2018-0009817

(51) Int. Cl.
*A61B 10/02* (2006.01)
*A61B 10/04* (2006.01)

(52) U.S. Cl.
CPC ...... *A61B 10/0275* (2013.01); *A61B 10/0283* (2013.01); *A61B 2010/045* (2013.01)

(58) Field of Classification Search
CPC . A61B 10/0275; A61B 10/0283; A61B 10/02; A61B 2010/045
See application file for complete search history.

(56) References Cited

U.S. PATENT DOCUMENTS

| 4,924,878 A | * | 5/1990 | Nottke | ............... | A61B 10/0275 600/564 |
| 5,172,701 A | | 12/1992 | Leigh | | |
| 5,752,923 A | * | 5/1998 | Terwilliger | ........ | A61B 10/0266 600/562 |
| 6,126,617 A | * | 10/2000 | Weilandt | ............ | A61B 10/0266 600/567 |

(Continued)

FOREIGN PATENT DOCUMENTS

| KR | 10-2013-0079788 | 7/2013 |
| KR | 101551311 | 9/2015 |
| KR | 101687099 | 12/2016 |

OTHER PUBLICATIONS

KIPO; Office Action dated Dec. 10, 2018 in Application No. 10-2017-0012789.

(Continued)

*Primary Examiner* — Rene T Towa
(74) *Attorney, Agent, or Firm* — Snell & Wilmer L.L.P.

(57) ABSTRACT

Provided is a cutting biopsy instrument facilitating loading by minimizing a change in a grip on a biopsy instrument and enhancing tissue sampling accuracy and safety and simplifying collection of sampled tissue by proposing a new shift relation between an stylet and an cannula at the shooting of the needles.

6 Claims, 26 Drawing Sheets

(56) References Cited

U.S. PATENT DOCUMENTS

| | | | |
|---|---|---|---|
| 7,041,065 B2* | 5/2006 | Weilandt | A61B 10/0233 600/567 |
| 8,460,330 B2 | 6/2013 | Nicholls et al. | |
| 2006/0195044 A1 | 8/2006 | Cooke et al. | |
| 2007/0213635 A1* | 9/2007 | Hancock | A61B 10/0275 600/567 |
| 2008/0200833 A1* | 8/2008 | Hardin | A61B 10/0275 600/566 |
| 2008/0281226 A1* | 11/2008 | Peters | A61B 10/0275 600/567 |
| 2009/0082696 A1* | 3/2009 | Nicoson | A61B 10/0275 600/566 |
| 2015/0057571 A1 | 2/2015 | Gundberg | |
| 2015/0305721 A1 | 10/2015 | Kang et al. | |

OTHER PUBLICATIONS

KIPO; Notice of Allowance dated Apr. 30, 2019 in Application No. 10-2017-0012789.
WIPO; International Search Report and Written Opinion dated Aug. 2, 2018 in Application No. PCT/KR2018/001177.

* cited by examiner

CUTTING BIOPSY INSTRUMENT

CROSS-REFERENCE TO RELATED APPLICATIONS

This application is the national stage entry of International Application No. PCT/KR2018/001177 filed on Jan. 26, 2018, which claims priority to Korean Patent Application No. 10-2017-0012789 filed on Jan. 26, 2017 and Korean Patent Application No. 10-2018-0009817 filed on Jan. 26, 2018; the contents of each of the respective applications are incorporated herein by reference in their entireties.

TECHNICAL FIELD

The present disclosure relates to a cutting biopsy instrument.

BACKGROUND ART

In general, for the examination of biological tissue, a method of inserting an instrument for sampling the biological tissue into the biological tissue and collecting sampling target tissue from the biological tissue is used. This type of method includes an aspiration biopsy and a cutting biopsy.

Recently, cutting biopsies, by which tissue may be acquired preserving the histological architecture thereof by cutting out the tissue using a needle and diagnostic accuracy may be increased, have been widely used. Cutting biopsies allow the diameter of a needle inserted into an affected part and repetitive invasive procedures to be minimized and allow a precise procedure to be performed for small-size sampling and are thus more widely used than aspiration biopsies.

In a biopsy device, which uses a cutting biopsy and is disclosed in Korea Patent Publication 10-1463867 or 10-1551311, an stylet is shooted prior to an cannula in a cutting mechanism, and accordingly, the stylet, which is very thin, may not penetrate dense epithelium tissue or hard calcified tissue or may be bent while advancing. As a result, a tuber may be pushed back or the stylet may not reach an exact area of target tissue, causing difficulties in a procedure.

Meanwhile, techniques for increasing accuracy, including a technique using an ultrasonic waveguide to enable a needle set to accurately reach target tissue, have been greatly developed. However, according to the related art, a practitioner usually changes his/her grip on a biopsy instrument or uses both hands when loading the biopsy instrument, and therefore, the targeting of an ultrasonic waveguide may be disturbed particularly when repetitive sampling is required.

Therefore, there has been an increasing need for a technique for enabling a practitioner to perform single sampling and repetitive sampling at a time with only one hand gripping a biopsy instrument without changing his/her grip on the biopsy instrument when the practitioner grips and handles an ultrasonic waveguide with one hand and the biopsy instrument with the other hand and for facilitating collection of sampled tissue.

DESCRIPTION OF EMBODIMENTS

Technical Problem

Provided is a biopsy instrument having a loading and shooting structure that facilitates loading by minimizing a change in a grip of only one hand on a biopsy instrument and facilitates a change in a loading pattern for a small or large sample size.

Provided is also a new shift relation between an stylet and an cannula at the shooting of the needles, thereby removing difficulties occurring in a procedure when a tuber is pushed back or an stylet does not reach an exact area of sampling target tissue because the stylet does not penetrate dense epithelium tissue or hard calcified tissue or is bent when the stylet is shooted forward.

Provided is also a technique for facilitating collection of tissue sampled using a biopsy instrument.

Solution to Problem

According to an aspect of the present disclosure, a cutting biopsy instrument includes a housing extending in an axis direction and including a hollow portion extending in a length direction of the housing and at least one opening communicating with the hollow portion; a needle set including an stylet and an cannula and being partially arranged in the hollow portion, the stylet having a tissue sampling groove at an end, and the cannula having a pipe shape to receive the stylet therein and being shorter than the stylet; a master block connected to an end of the cannula, penetrated by the stylet, and arranged in the hollow portion; a hub block penetrated by the stylet, arranged in the hollow portion, and aligned with the master block in the axis direction; a first spring arranged in the hollow portion, aligned with the master block and the hub block in the axis direction, and providing the master block with a first elastic force in a direction parallel with the axis direction; a second spring arranged in the hollow portion, aligned with the master block, the hub block, and the first spring in the axis direction, and providing the hub block with a second elastic force in the direction parallel with the axis direction; a first holding unit arranged in the housing and provided to selectively engage with the master block to provide resistance against the first elastic force to the master block; a second holding unit arranged in the housing and provided to selectively engage with the hub block to provide resistance against the second elastic force to the hub block; a loading unit including a first handle provided to be coupled to the housing to apply a force to the hub block in a first direction; and a shooting unit arranged at the housing and provided to selectively disengage the master block from at least the first holding unit.

The cutting biopsy instrument may further include a locking unit arranged between an end of the first handle and the housing and provided to selectively fasten the end of the first handle to the housing, wherein the first handle may have an elastic force in a direction opposite the locking unit.

The cutting biopsy instrument may further include a stopper arranged at at least one portion selected from an end of the first handle and a portion of the housing adjacent to the first handle and provided to restrain a rotation angle of the first handle.

The cutting biopsy instrument may further include an extension unit extending from the hub block toward the second spring and provided to block the at least one opening of the housing in at least one state.

The cutting biopsy instrument may further include a connecting bar embedded in the master block, provided to move in a length direction of the master block, coupled to the end of the cannula, and including a second handle exposed outside the master block, wherein the master block may include a third holding unit selectively inhibiting a motion of the connecting bar.

The master block may include a releasing unit extending toward the hub block and provided to release the resistance of the second holding unit.

Other aspects, features, and advantages than those described above will be clear from the accompanying drawings, the claims, and the description of embodiments below.

Advantageous Effects of Disclosure

According to an embodiment, a user operates a loading unit by applying a grasping force to a biopsy instrument having a reciprocating motion structure in which an cannula retreats from an stylet and then advances after the cannula and the stylet are inserted into a body in a loaded state, in which a first spring and a second spring are pushed backward to have a restoring force. Accordingly, the biopsy instrument may have a loading and shooting structure that facilitates single loading or multiple loadings by minimizing a change in the grip of only one hand on the biopsy instrument and facilitates a change in a loading pattern for a small or large sample size and may remove difficulties occurring in a procedure when a tuber is pushed back or the stylet does not reach an exact area of sampling target tissue because the stylet does not penetrate dense epithelium tissue or hard calcified tissue or is bent when the stylet is shooted forward.

When an ultrasonic waveguide is used, a user may perform loading and shooting with only one hand while holding the ultrasonic waveguide with the other hand, and accordingly, the biopsy instrument enables targeting to be exactly maintained, thereby increasing the accuracy of a procedure.

Due to the coupling structure between an cannula connecting bar, to which the cannula is fixed, and the master block, tissue in a tissue sampling groove of the stylet may be simply collected after tissue sampling by just moving the cannula connecting bar without any other special operation. Accordingly, simple sample collection may be achieved with one hand.

Meanwhile, an additional function may be realized by increasing the length and the size of a portion of the master block in an advancing direction to allow the master block to move in a hollow portion in tight contact with a housing. Since the master block may perform a stable sliding motion, a precise procedure may be accomplished.

MODE OF DISCLOSURE

Figure 1:
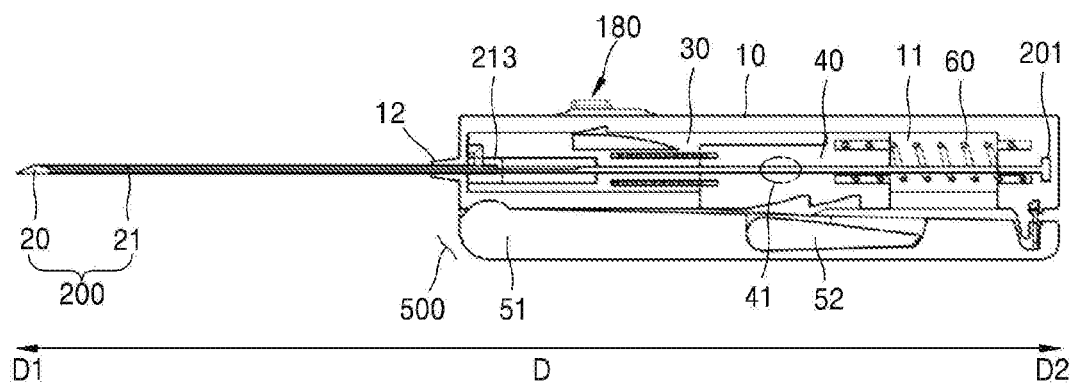
FIG. 1 is an assembled cross-sectional view of a cutting biopsy instrument according to an embodiment of the present disclosure.

Hereinbelow, various embodiments and/or modes are shown and described with reference to the drawings. For the purpose of explanation, a variety of specific details are described to promote understanding one or more modes. However, it will be recognized by one of ordinary skill in the art that such mode(s) can be implemented without these specific details. The descriptions below and the attached drawings show in detail particular example modes of one or more modes. However, these modes are examples, and some of various methods based on the principles of various modes may be used, and the descriptions below are intended to include all these modes and equivalents.

In addition, various modes and features will be presented by systems that may include devices, components, and/or modules. It will be appreciated and understood that various systems may include additional devices, components, and/or modules and/or may not include all of devices, components, and modules described with reference to the drawings.

It may not be interpreted that the terms "embodiment", "example", "mode", "illustration", etc. used herein specify that a stated mode or design is better or more advantageous than other modes or designs. It will be further understood that the terms "comprises" and/or "comprising" specify the presence of relevant features and/or components, but do not preclude the presence or addition of one or more other features, components, and/or groups thereof.

While terms including ordinal numbers such as "first," "second," etc., may be used to describe various components, such components must not be limited to the above terms. The above terms are used only to distinguish one component from another. For example, a first component could be termed a second component, and, similarly, a second component could be termed a first component without departing from the scope of the present disclosure. The term "and/or" includes combinations of a plurality of associated listed items or one of the associated listed items.

Unless otherwise defined, all terms (including technical and scientific terms) used herein have the same meaning as commonly understood by one of ordinary skill in the art to which the present disclosure belongs. It will be understood that terms, such as those defined in commonly used dictionaries, should be interpreted as having a meaning that is consistent with their meaning in the context of the relevant art, and will not be interpreted in an idealized or overly formal sense unless expressly so defined herein.

Some components are omitted, enlarged, or reduced in the drawings to explain the functions of each component, but it will be understood that the details shown in the drawings do not limit the technical features and scope of the present disclosure.

In the descriptions below, a technical feature or a component will be described with reference to a plurality of drawings together.

Referring to FIGS. 1, 3, 5, 6, and 9, a cutting biopsy instrument according to an embodiment of the present disclosure includes a housing 10, which extends in parallel with an axis D and has a hollow portion 11.

Figure 3:
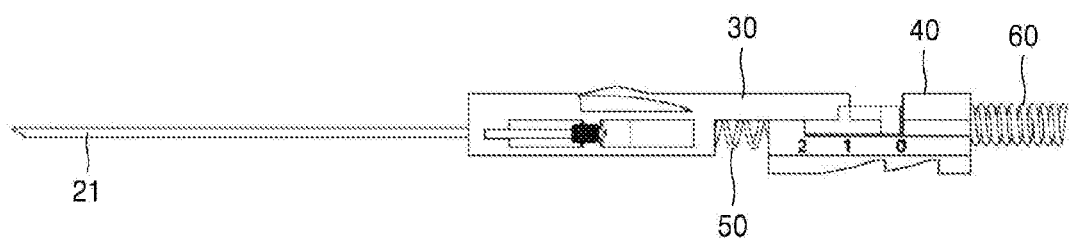
FIG. 3 is a diagram for explaining the combined state of an cannula, a master block, and a drive unit, according to an embodiment of the present disclosure.

The cutting biopsy instrument may include a master block 30. Referring to FIGS. 1 and 3, the master block 30 may be connected to an end 213 of an cannula 21 in a second direction D2 opposite a first direction D1, may be longer in a direction parallel with the axis D than in a direction perpendicular to the axis D, and may perform a reciprocating motion in the hollow portion 11 in the direction parallel with the axis D.

The cutting biopsy instrument may include a drive unit including a first spring 50, a hub block 40, and a second spring 60, which are sequentially arranged in a line in the hollow portion 11. The first spring 50 is connected to the master block 30, and a needle set penetration portion 41 is formed in the hub block 40.

The cutting biopsy instrument may include a loading unit 500. The loading unit 500 may include a connector 52, which has a variable position at which the connector 52 is caught in the hub block 40, and a first handle 51, which is connected to the connector 52 and gives a force to the connector 52 in the second direction D2.

Figure 6:
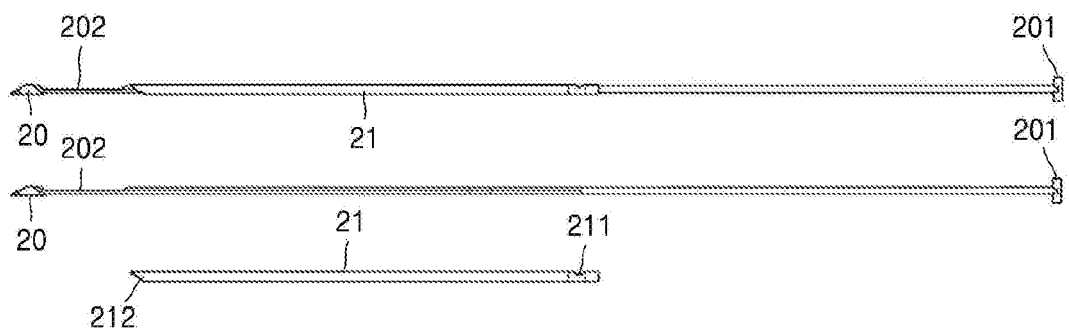
FIG. 6 is a diagram for explaining the structure of a needle set, according to an embodiment of the present disclosure.
Figure 9:
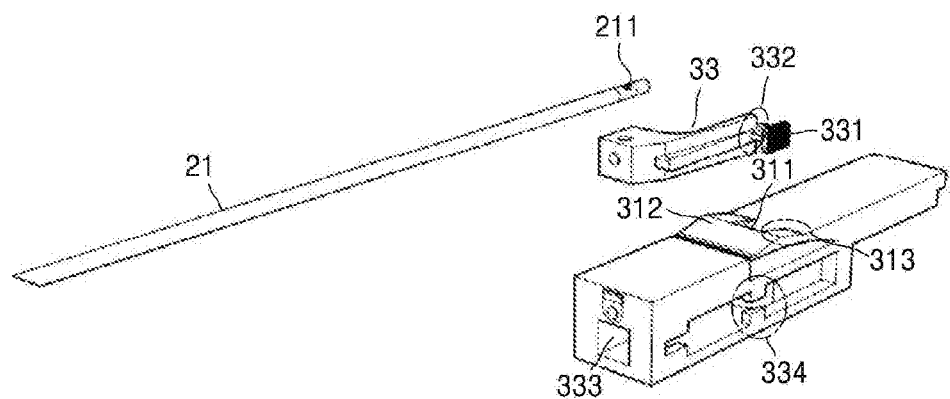
FIG. 9 is an exploded view of an cannula and a master block, according to an embodiment of the present disclosure.

Referring to FIGS. 1, 6, and 9, a needle set 200 may include an stylet 20 and the cannula 21.

Referring to FIG. 6, the stylet 20 having a tissue sampling groove 202 at an end. The tissue sampling groove 202 has a groove structure which is open upwards or downwards. The stylet 20 may be provided to penetrate the housing 10 along the axis direction D, and an opposite end 201 of the stylet 20 may be fixed to an end portion of the housing 10 in the second direction D2.

The cannula 21 has a pipe shape to accommodate the stylet 20 therein and is shorter than the stylet 20. The cannula 21 has a blade 212 at an end to cut tissue held in the tissue sampling groove 202 and may perform a reciprocating motion with respect to the stylet 20.

The needle set 200 may pass through the housing 10 and protrude outwards through a hole 12 in a front end of the housing 10. Accordingly, a portion of the needle set 200 is arranged in the hollow portion 11.

Although not shown, according to an embodiment, a certain space may be formed between the cannula 21 and the stylet 20 and connected to the tissue sampling groove 202. A hole 211 may be formed in an opposite end of the cannula 21 to be perpendicular to the axis direction D and to communicate with the space inside the cannula 21. Negative pressure may be created in the inner space of the cannula 21 via the hole 211 during the movement of the master block 30.

At least the cannula 21 of the needle set 200 may be coupled to the master block 30. The master block 30 is arranged in the hollow portion 11. The stylet 20 may be provided to penetrate the master block 30.

Figure 2:
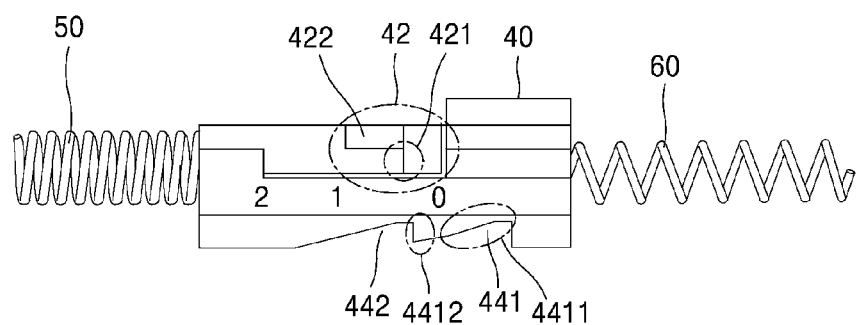
FIG. 2 is a diagram for explaining an example of an assembled drive unit, according to an embodiment of the present disclosure.
Figure 4:
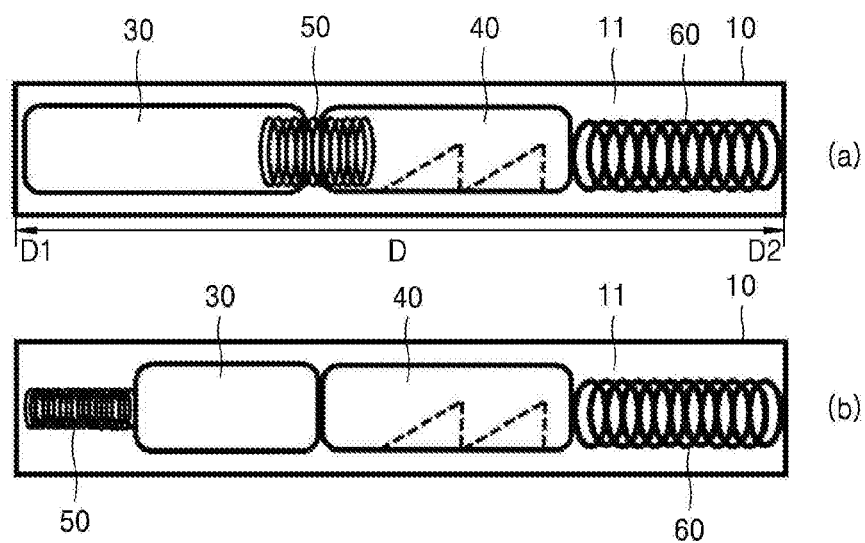
FIG. 4 is a schematic diagram for explaining examples of the arrangement of a drive unit, according to an embodiment of the present disclosure.

According to an embodiment, as shown in FIG. 2 and FIG. 4(a), the first spring 50 may be an extension spring fixed between the master block 30 and the hub block 40. The second spring 60 may be a compression spring between the hub block 40 and an end of the housing 10. Accordingly, in this case, a first elastic force and a second elastic force may both act in the first direction D1.

According to this embodiment, when only the hub block 40 is moved in the second direction D2 and then fixed during loading while the master block 30 is fixed, both the first spring 50 and the second spring 60 come to have an elastic force in the first direction D1. Thereafter, when the fixation of the master block 30 in the hollow portion 11 is released via manipulation of a shooting unit 180, the master block 30 is moved in the second direction D2 by a restoring force of the first spring 50 since the hub block 40 is still fixed in the hollow portion 11. Thereafter, when the fixation of the hub block 40 is released as the master block 30 contacts the hub block 40, the master block 30 and the hub block 40 are simultaneously moved in the first direction D1 by a restoring force of the second spring 60. With the movement of the master block 30 in the second direction D2 and the movement of the master block 30 in the first direction D1, the cannula 21 coupled to the master block 30 is simultaneously moved along with the master block 30, and accordingly, tissue may be taken into the tissue sampling groove 202.

According to another embodiment, as shown in FIG. 4(b), the first spring 50 is provided, as a compression spring compressed to a certain degree, to connect and couple the master block 30 to an end of the hollow portion 11 in the first direction D1. The second spring 60 is provided, as a compression spring not compressed or compressed to a small degree, to connect and couple the hub block 40 to an end of the hollow portion 11 in the second direction D2 and to separate the hub block 40 from the master block 30, wherein the compression spring has a greater elastic force than the first spring 50. At this time, an elastic force of the second spring 60 may be greater than that of the first spring 50.

According to this embodiment, when only the hub block 40 is moved in the second direction D2 and then fixed with the master block 30 fixed during loading, both the first spring 50 and the second spring 60 are compressed such that the first spring 50 comes to have an elastic force in the second direction D2 and the second spring 60 comes to have an elastic force in the first direction D1. Thereafter, when the fixation of the master block 30 in the hollow portion 11 is released via manipulation of the shooting unit 180, the master block 30 is moved in the second direction D2 by a restoring force of the first spring 50. Thereafter, when the fixation of the hub block 40 is released as the master block 30 contacts the hub block 40, the master block 30 and the hub block 40 are simultaneously moved in the first direction D1 by a restoring force of the second spring 60, which is greater than the restoring force of the first spring 50. With the movement of the master block 30 in the second direction D2 and the movement of the master block 30 in the first direction D1, the cannula 21 coupled to the master block 30 is simultaneously moved along with the master block 30, and accordingly, tissue may be taken into the tissue sampling groove 202.

Figure 5:
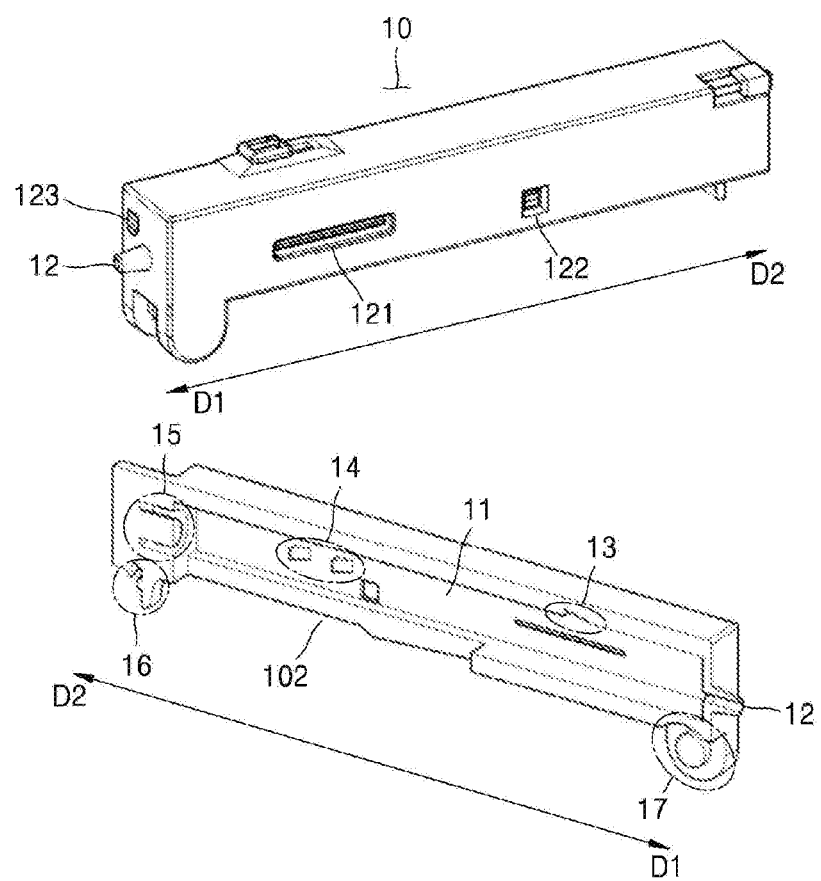
FIG. 5 is a diagram for explaining the structure of a housing, according to an embodiment of the present disclosure.

The detailed structure of the housing 10 is examined with reference to FIG. 5. Referring to FIG. 5, the housing 10 includes a first holding unit 13, which is formed in at least one side of the hollow portion 11 to fix the master block 30 during loading.

Meanwhile, the housing 10 may include a second holding unit 14, which is formed in another side of the hollow portion 11 to fix the hub block 40. Additionally, the housing 10 may have a recess as a second spring engaging portion 15 to fix the second spring 60.

Figure 7:
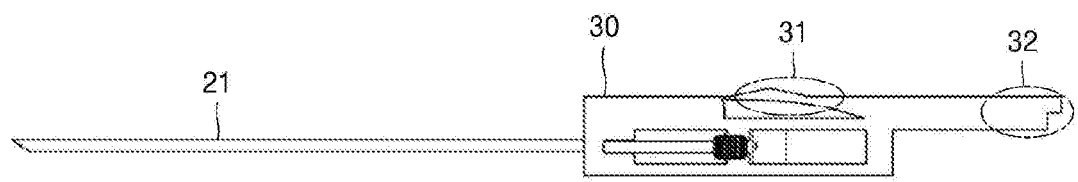
FIG. 7 is a diagram of the combination between an cannula and a master block, according to an embodiment of the present disclosure.

Referring to FIGS. 7 and 9, an example of the detailed structure of the master block 30 may be checked. The master block 30 includes a first fixing unit 31, which is elastic and to which the cannula 21 is fixed.

The first fixing unit 31 is provided to have an elastic force in a direction perpendicular to the axis direction D. The first fixing unit 31 maintains a restoring force acting upward in FIG. 7 and thus engages with the first holding unit 13 in a default state, i.e., a restored state. Accordingly, in spite of the restoring force of the first spring 50, the master block 30 is fixed without a movement in the hollow portion 11.

When a pressing force is applied to the first fixing unit 31, the first fixing unit 31 is disengaged from the first holding unit 13, and the master block 30 is moved in the second direction D2 by the restoring force of the first spring 50.

Thereafter, the master block 30 and the hub block 40 are moved in the first direction D1 by the restoring force of the second spring 60. At this time, when the restoring force of each of the first spring 50 and the second spring 60 is set, the first fixing unit 31 is moved toward the first holding unit 13 while being pressed due to the shape thereof and then released from the pressed state so as to elastically move upward, and accordingly, the first fixing unit 31 re-engages with the first holding unit 13 and the first spring 50 remains in a ready state prior to loading.

The first fixing unit 31 may include a first engaging point 311, at which the first fixing unit 31 engages with the first holding unit 13 in the default state, and first pressing points 312 and 313, which transmit a pressing force of the shooting unit 180 so as to release the engagement between the first engaging point 311 and the first holding unit 13.

Meanwhile, as shown in FIGS. 7 and 9, the first pressing points 312 and 313 may be provided in opposite directions, respectively, due to the slope structure of the first fixing unit 31. It is apparent that the configuration of the first pressing points 312 and 313 may vary with the type and operation of the shooting unit 180.

Figure 8:
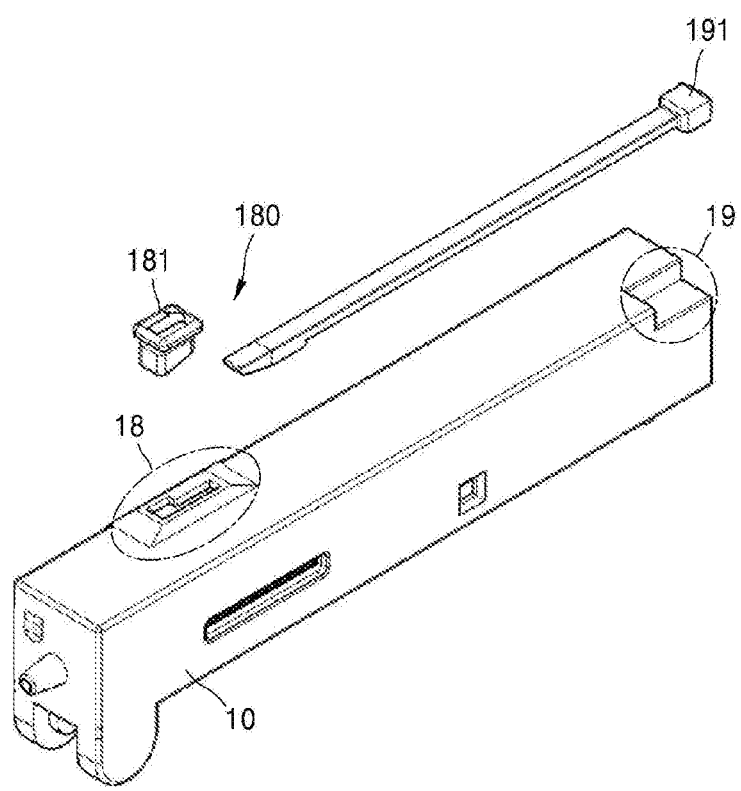
FIG. 8 is an exploded view for explaining the structure of a housing and a shooting unit, according to an embodiment of the present disclosure.

Referring to FIG. 8, according to an embodiment, the shooting unit 180 may include a first shooting unit 181 and a second shooting unit 191. The first shooting unit 181 may be provided to be movable both ways through a first guide hole 18, which is formed in a top surface of the housing 10 in a direction inserted into the hollow portion 11.

Figure 18:
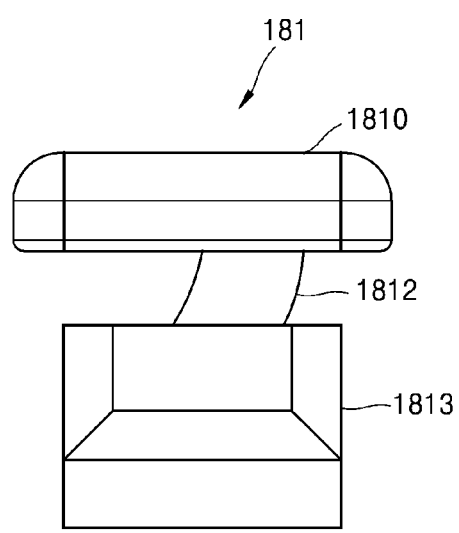
FIG. 18 is a diagram for explaining an example of the structure of a first shooting unit.

At this time, to prevent a shooting error, the first guide hole 18 has a "-ㅜ" shape bent in perpendicular direction. Referring to FIG. 18, the first shooting unit 181 includes a head 1810, a connecting elastic body 1812, and a body 1813.

The connecting elastic body 1812 is moved along the first guide hole 18. The connecting elastic body 1812 is configured to have an elastic force to be pressed after traversing along the first guide hole 18 in a wide space at an end of the first guide hole 18 in the first direction D1.

The head 1810 is provided to protrude such that a practitioner may apply a pressing force to the head 1810 with a finger or the like, and the body 1813 is configured to press the first pressing point 312.

Figure 14:
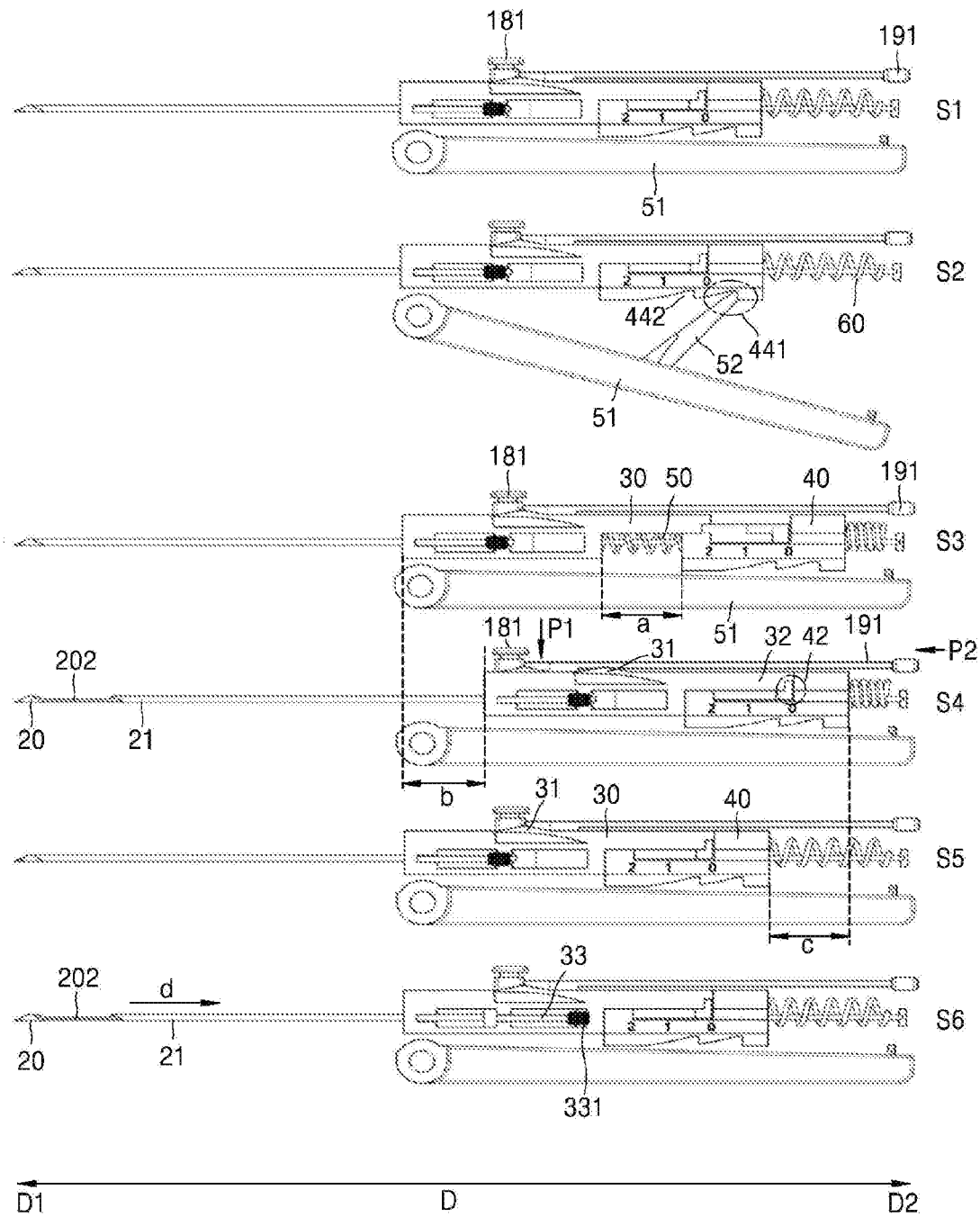
FIG. 14 is a diagram for explaining the operation of a cutting biopsy instrument, according to an embodiment of the present disclosure.
Figure 16:
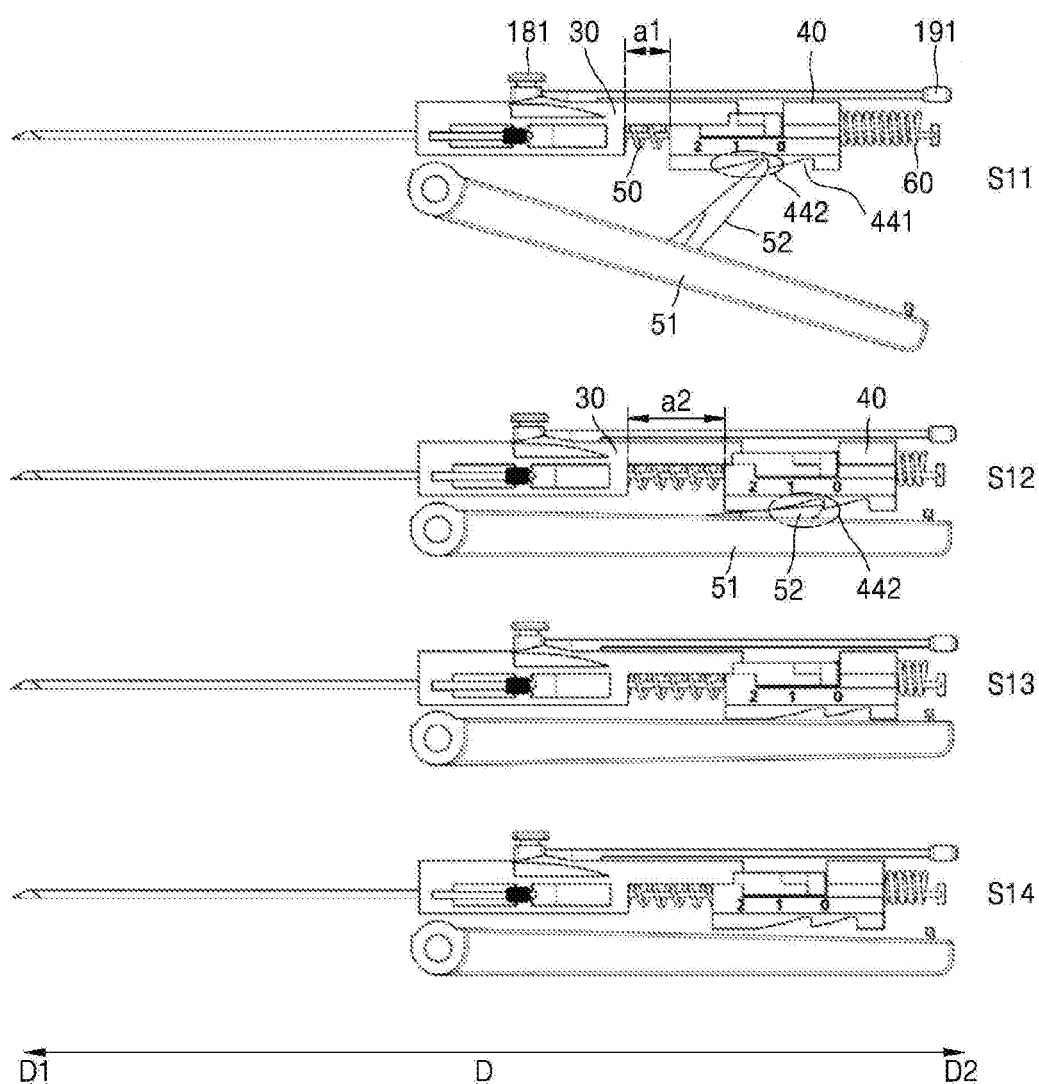
FIG. 16 is a diagram for explaining the operation of a cutting biopsy instrument during a loading procedure, according to an embodiment of the present disclosure.

The second shooting unit 191 is configured to apply a pressing force to the first pressing point 313. As shown in FIGS. 8, 14, and 16, the second shooting unit 191 is inserted into the hollow portion 11 from an end of the housing 10 in the second direction D2, along a guide line (not shown) formed in the hollow portion 11 along the axis direction D, so as to perform a reciprocating motion along the axis direction D. For the structure described above, a second guide hole 19 may be formed to penetrate the housing 10 so as to be connected to the hollow portion 11.

The second shooting unit 191 may perform the same function as the first shooting unit 181 by pressing the first pressing point 313, as described above. In other words, the first shooting unit 181 and the second shooting unit 191 may work as a configuration for achieving an effect of performing shooting to initiate the retreating and advancing movement of the cannula 21 such that when a practitioner grips the housing 10 for a procedure, a grip pattern change is minimized regardless of the practitioner's grip pattern.

It is not necessary to simultaneously provide both of the first shooting unit 181 and the second shooting unit 191. The first shooting unit 181 and the second shooting unit 191 may be selectively provided.

Figure 13:
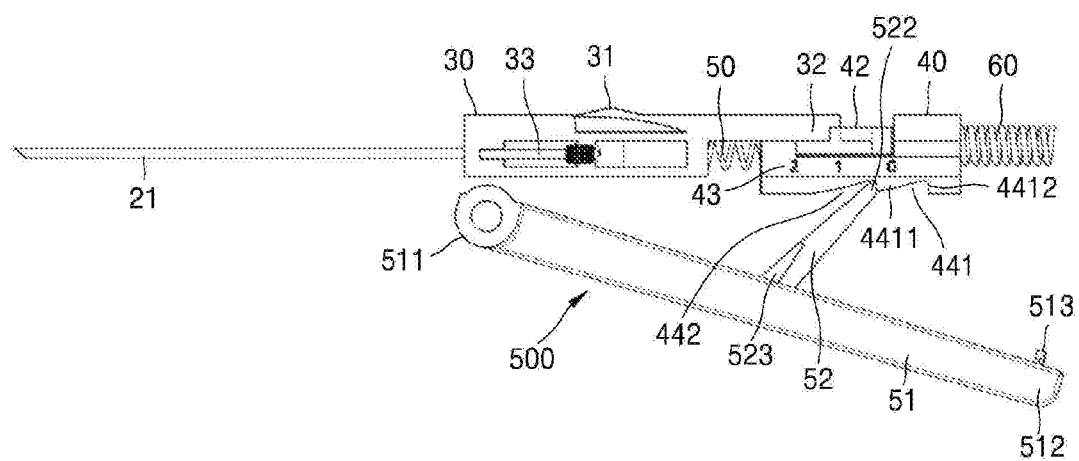
FIG. 13 is a diagram for explaining the assembled state of a cutting biopsy instrument except for a housing, according to an embodiment of the present disclosure.

Referring to FIGS. 7 and 13, a releasing unit 32 may be formed in an end region of the master block 30 in the second direction D2. The releasing unit 32 has a wing bar shape and protrudes in the second direction D2 from a main body region of the master block 30. The releasing unit 32 may have a bar shape to release the fixation of the hub block 40 to the second holding unit 14.

Figure 10:
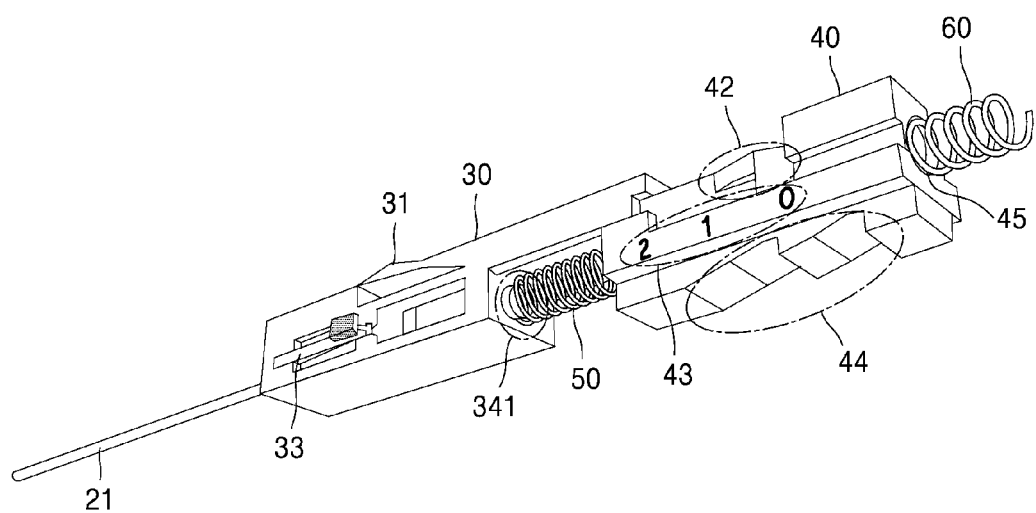
FIG. 10 is a diagram for explaining the combined state of an cannula, a master block, and a drive unit, according to an embodiment of the present disclosure.
Figure 11:
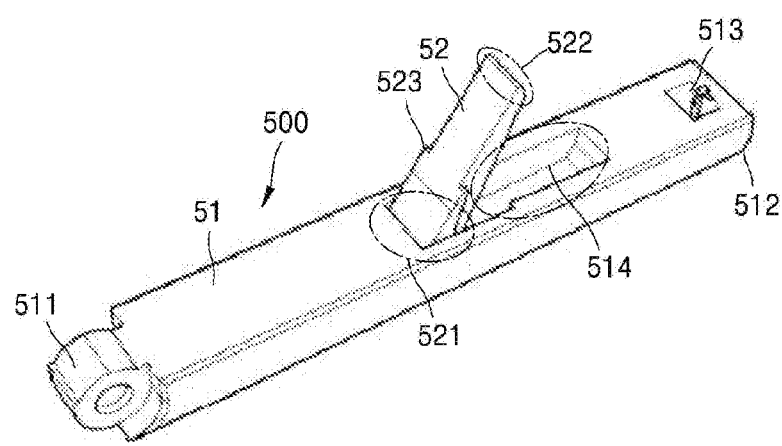
FIG. 11 is a perspective view of a loading unit according to an embodiment of the present disclosure.

Referring to FIGS. 2, 10, and 13, a second fixing unit 42 is formed in the hub block 40. The second fixing unit 42 may be caught in the second holding unit 14. During loading, the hub block 40 retreats and the second fixing unit 42 slides into the second holding unit 14. In a loaded state, the second fixing unit 42 is caught in the second holding unit 14 such that the hub block 40 is inhibited from advancing in the first direction D1 and has a fixed position in relation to the hollow portion 11.

When the master block 30 is retreated in the second direction D2 by the restoring force of the first spring 50 during shooting, the releasing unit 32 applies a pressing force to the second fixing unit 42, thereby releasing the engagement between the second fixing unit 42 and the second holding unit 14. As a result, the hub block 40 is shifted in the first direction D1 by the restoring force of the second spring 60 while pushing the master block 30 in the first direction D1, and accordingly, the cannula 21 is moved in the first direction D1, thereby cutting tissue and allowing the tissue to be hermetically accommodated in the tissue sampling groove 202 of the stylet 20.

To perform the function described above, the second fixing unit 42 of the hub block 40 may have elasticity.

Referring to FIG. 2, the second fixing unit 42 may include a second engaging point 421 and a second pressing point 422. The second engaging point 421 may be caught in the second holding unit 14 in the loaded state, and a pressing force of the releasing unit 32 may be applied to the second pressing point 422 such that the engagement between the second engaging point 421 and the second holding unit 14 may be released. The second fixing unit 42 may include a slope section, in which a connection point between the second engaging point 421 and the second pressing point 422 is the most protruding point, and may be configured such that the second engaging point 421 is caught in the second holding unit 14 via a space at a side of the second engaging point 421 in the first direction D1, excluding the second pressing point 422, as shown in FIG. 2.

In addition, the releasing unit 32 may provide a pressing force while moving along the slope section, and accordingly, the second fixing unit 42 may be pressed and disengaged from the second holding unit 14.

Referring to FIG. 10, for connection between the first spring 50 and the master block 30 and connection between the second spring 60 and the hub block 40, recesses are respectively formed, as spring receiving portions 341 and 45, in the master block 30 and the hub block 40 to respectively receive the first spring 50 and the second spring 60, which are adjacently connected to the master block 30 and the hub block 40, respectively.

As described above, since the master block 30 and the hub block 40 may contact each other and may contact an inner surface of the housing 10 in the hollow portion 11, a shock absorber (not shown) may be formed in at least one end of each of the master block 30 and the hub block 40 along the axis direction D.

Referring to FIGS. 2, 10, and 13, a configuration for guiding the hub block 40 that is retreated in the second direction by the loading unit 500 may be provided. For the configuration, the hub block 40 may include sawteeth 441 and 442 each having a first slope 4412, in which the connector 52 is caught, and a second slope 4411, on which the connector 52 slides when the connector 52 returns to an original state via a restoring force. As described above, two sawteeth 441 and 442 may be formed in an embodiment to allow the cannula 21 to be loaded with different retreating and advancing distances such that the size of tissue is control, which will be described below. The present disclosure is not limited to this embodiment, but the number of sawteeth may be changed according to design conditions. Although the sawteeth 441 and 442 are concave teeth in the drawings, the sawteeth 441 and 442 may have any shape as long as the sawteeth 441 and 442 can perform their function.

As shown in the drawings, the first slope 4412 is nearly at a right angle, and the second slope 4411 has a gentle grade. Accordingly, as described above, a force acting when an end 522 of the connector 52 moves in the second direction D2 is fully transmitted to the hub block 40 such that the hub block 40 moves against the restoring force of the first and second springs 50 and 60.

In addition, the connector 52 may contact and slide on the second slope 4411 during multiple times of loading. At this time, the second slope 4411 is configured to have a gentle grade such that the movement of the end 522 of the connector 52 is not restricted.

Referring to FIGS. 5, 11, 12, 13, and 17, an end 511 of a first handle 51 included in the loading unit 500 may be fixed to a hinge portion 17 of the housing 10, and an opposite end 512 of the first handle 51 may be open, that is, may not be fixed. The end 511, i.e., a portion hinge-fixed to the housing 10, may include a first elastic body (not shown) that provides a stretching force such that the opposite end 512 of the first handle 51 is separated from the housing 10 in a restored state. Such first elastic body may be implemented using a ring spring or the like but is not limited thereto.

Accordingly, unless the movement of the first handle 51 is inhibited by locking devices 16 and 513 described below, the first handle 51 rotates around the end 511 so as to be separated from the housing 10 such that the opposite end 512 may be maintained to be separated from the housing 10 by a maximum distance. A hinge connector connected to the housing 10 at the end 511 of the first handle 51 may include a trapping member (e.g., a sawtooth) such that the first handle 51 is prevented from being separated from the housing 10 by a distance more than required and the end 522 of the connector 52 is definitely caught in the sawteeth 441 and 442.

An end 521 of the connector 52 included in the loading unit 500 may be hinge-fixed to a region between the ends 511 and 512 of the first handle 51, and an opposite end, i.e., the end 522 of the connector 52 may be open, that is, may not be fixed in a direction in which the opposite end 522 is caught in the sawteeth 441 and 442. Similarly to the first handle 51 described above, a portion of the connector 52, which is hinge-fixed to the first handle 51, may include a second elastic body (not shown) that provides a stretching force such that the opposite end 522 of the connector 52 is separated from the first handle 51 and is caught in the sawteeth 441 and 442 in the restored state. Such second elastic body may be implemented using a ring spring or the like but is not limited thereto.

Accordingly, unless the movement of the connector 52 is inhibited by the locking devices 16 and 513 described below, the connector 52 may be separated from the first handle 51 around the end 521 such that the opposite end 522 may be maintained to be separated from the first handle 51 by a maximum distance. Similarly to the hinge connector at the end 511 of the first handle 51, the end 521 of the connector 52, i.e., a hinge connector connected to the first handle 51, may include a trapping member (e.g., a sawtooth) such that the connector 52 is prevented from being separated from the first handle 51 by a distance more than required and the opposite end 522 of the connector 52 is definitely caught in the sawteeth 441 and 442.

Figure 12:
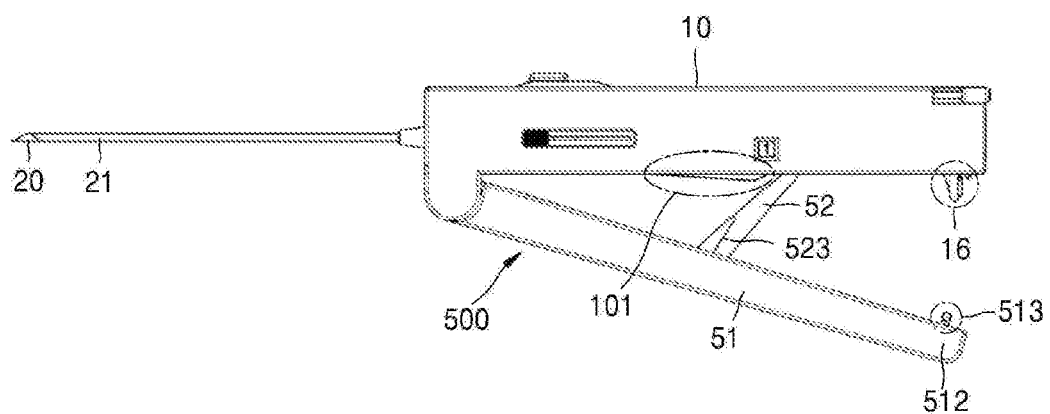
FIG. 12 is a diagram of the assembled state of a cutting biopsy instrument, according to an embodiment of the present disclosure.

Referring to FIG. 12, a sill 101 is formed on the housing 10. The sill 101 may be provided to connect the outside of the housing 10 to the hollow portion 11 and may be provided as a protrusion formed at an end of a guiding portion 102 (see FIG. 5), which guides an area in which the connector 52 engages with the sawteeth 441 and 442. When the loaded state is entered since the opposite end 522 of the connector 52 is moved in the second direction D2 by the hinge motion of the above-described mechanism, which is caused by a pressing force applied to the first handle 51, the sill 101 may allow the connector 52 to be separated from the sawteeth 441 and 442.

At this time, the sill 101 is configured such that a connector wing 523 is caught in the sill 101. When a pressing force is applied to the first handle 51, the opposite end 522 of the connector 52 provides the pressing force to push and move the hub block 40 in the second direction D2. At this time, due to the positions of the sawteeth 441 and 442 formed in the hub block 40, the second engaging point 421 of the second fixing unit 42 moves in the second direction D2 a little more over a position at which the second engaging point 421 strongly engages with the second holding unit 14. At this time, the connector wing 523 starts to contact the sill 101, and the connector 52 is moved to be separated from the sawteeth 441 and 442. At this time, when the first handle 51 is pressed to the full, the opposite end 522 of the connector 52 is separated and disengaged from the sawteeth 441 and 442.

In this state, the hub block 40 is a little moved forward in the first direction D1 and is firmly caught in the second holding unit 14.

Referring to FIGS. 5, 11, 12, 13, and 15, a cutting biopsy instrument according to an embodiment may include the locking devices 16 and 513, which toggle between a locked state and an unlocked state according to a pressing force when the opposite end 512 of the first handle 51 contacts the housing 10 as the pressing force is applied to the first handle 51, thereby controlling the coupling between the first handle 51 and the housing 10.

The locking devices 16 and 513 have a structure in which the locking device 16 in the first handle 51 may be coupled to the locking device 513 in the housing 10. The locking devices 16 and 513 are configured to be locked with a slight gap between the first handle 51 and the housing 10 when a pressing force is removed after the first handle 51 fully contacts the housing 10 as the pressing force is applied to the first handle 51 and to be unlocked when a pressing force is newly applied to the first handle 51 and then removed.

For the movement of the connector 52 when the connector 52 is lifted by the sill 101 according to the functional execution described above, a groove 514 may be formed in the first handle 51. As the connector 52 is received in the groove 514, the connector 52 may be prevented from being caught in the sawteeth 441 and 442 during the movement of the hub block 40.

Figure 17:
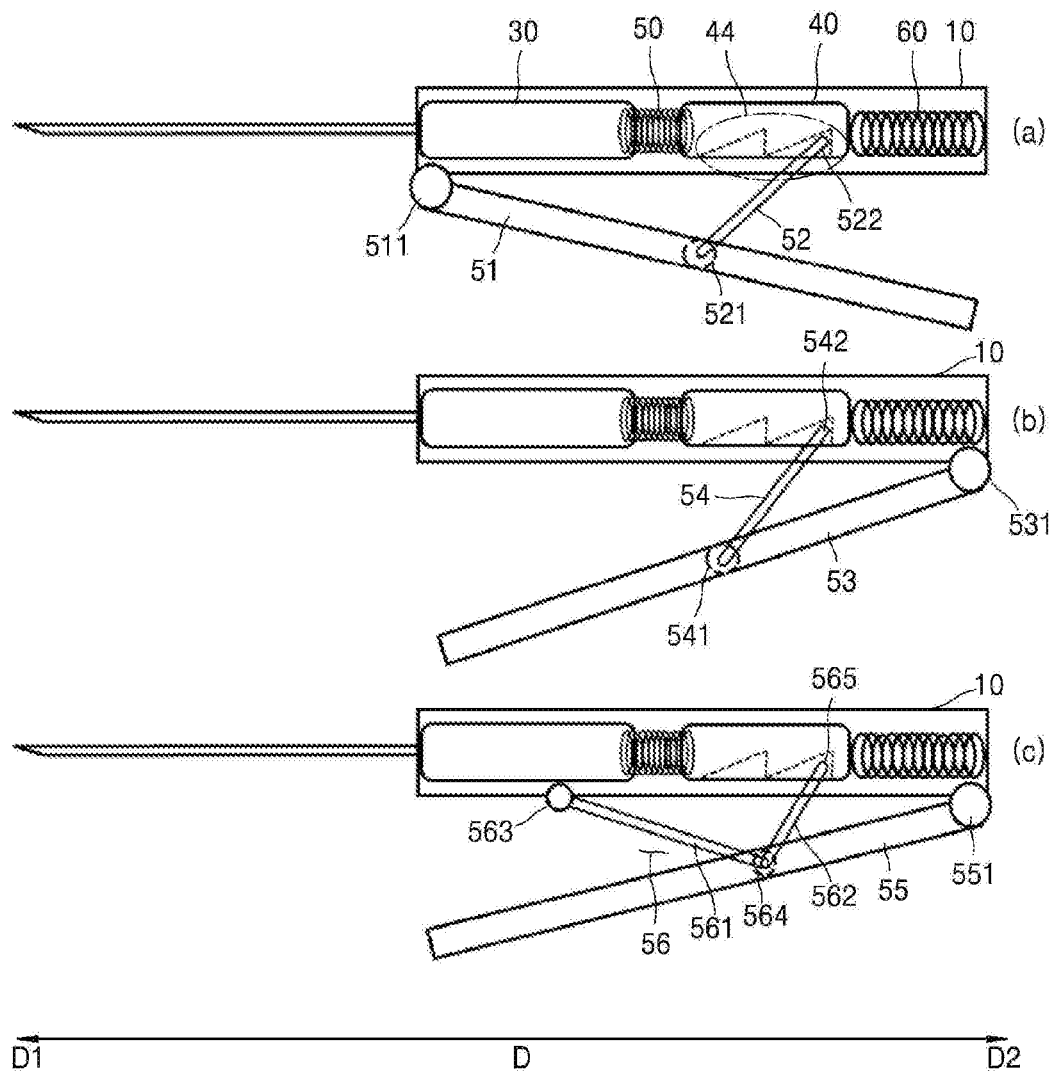
FIG. 17 is a diagram for explaining examples of a loading unit, according to an embodiment of the present disclosure.

Referring to FIG. 17, the first handle 51 and the connector 52 may be configured in various manners. Referring to FIG. 17(*a*), in the same structure as that described above, the end 511 of the first handle 51 is hinged to the housing 10, the end 521 of the connector 52 is hinged to the first handle 51, and the opposite end 522 of the connector 52 is in contact with sawteeth 44 of the hub block 40. Accordingly, when loading is performed, the master block 30, the first spring 50, the hub block 40, and the second spring 60 are driven.

Referring to FIG. 17(*b*), differently from FIG. 17(*a*), an end 531 of a first handle 53 in the second direction D2 is hinged to the housing 10, an end 541 of a connector 54 is hinged to the first handle 53, and an opposite end 542 of the connector 54 is in contact with the sawteeth 44 of the hub block 40. Accordingly, as described above with reference to FIG. 17(*a*), when loading is performed, the master block 30, the first spring 50, the hub block 40, and the second spring 60 are driven.

Referring to FIG. 17(*c*), differently from FIGS. 17(*a*) and 17(*b*), while an end 551 of a first handle 55 in the second direction D2 is hinged to the housing 10, similarly to FIG. 17(*b*), a connector 56 includes a first sub connector 561 and a second sub connector 562. An end 563 of the first sub connector 561 in the first direction D1 is hinged to the housing 10, and an opposite end 564 of the first sub connector 561 is connected to the second sub connector 562 and is hinged to the first handle 55. An opposite end 565 of the second sub connector 562 is in contact with the sawteeth 44 of the hub block 40. Similarly to FIG. 17(*b*) a loading force is apparently provided.

It may be seen in the drawings described above together with FIGS. 15 and 16 that at least two sawteeth 441 and 442 and at least two second holding units 14 are formed to have the same width as one another.

Figure 15:
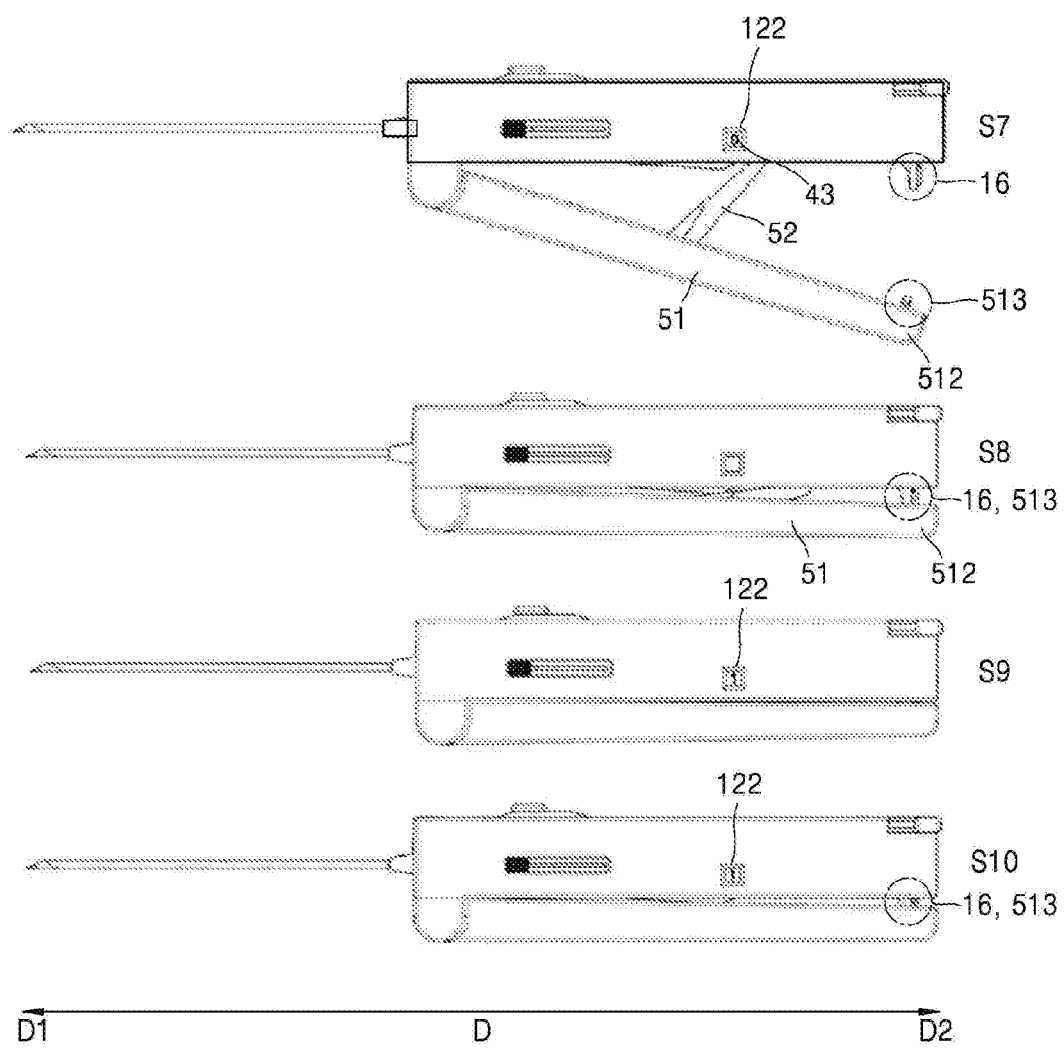
FIG. 15 is a diagram for explaining the operation of a cutting biopsy instrument during a loading procedure, according to an embodiment of the present disclosure.

In this case, referring to FIG. 15 first, when first loading is performed in a default state in stage S7 as a pressing force is applied to the first handle 51, that is, when a first pressing force is applied to the first handle 51, an opposite end of the connector 52 applies a force to a first sawtooth, i.e. the sawtooth 441 (see FIG. 13), which comes first when viewed from the second direction D2, in the second direction D2 such that the hub block 40 is moved. Thereafter, in stages S8 and S9 in which the first handle 51 is pressed to the maximum, according to the moving mechanism described above, when the locking devices 16 and 513 are locked with a gap between the first handle 51 and the housing 10 by releasing the pressing force, the hub block 40 is caught in and fixed to a first second holding unit (i.e., a trap portion of the second holding unit 14 in the first direction D1) (see FIG. 5), which comes first in the second direction D2, in a stage S10.

Thereafter, referring to FIG. 16, when the first handle 51 is pressed again to the maximum in the state S10 and then released, the opposite end of the connector 52 is in contact with and slides on a slope of the sawtooth 441, the slope being arranged in the second direction D2, and is then caught in a slope of the sawtooth 442 coming second viewed from the second direction D2, the slope of the sawtooth 442 being arranged in the first direction D1, in a recovered state S11. At this time, the hub block 40 is separated from the master block 30 by a distance "a1".

As a second loading is performed by reapplying a pressing force to the first handle 51 in stages S12 and S13, the opposite end of the connector 52 applies a force to a second sawtooth, i.e. the sawtooth 442, which comes second when viewed from the second direction D2, in the second direction D2 such that the hub block 40 is caught in and fixed to a second second holding unit (i.e., a trap portion of the second holding unit 14 in the second direction D2), which comes second in the second direction D2, in a stage S14. Accordingly, the hub block 40 may be separated from the master block 30 by a distance "a2". Therefore, in the case of the second loading, the hub block 40 further retreats in the second direction D2 than in the case of the first loading by the distance "a1", and accordingly, the restoring force of the first spring 50 and the second spring 60 is further enhanced.

As described above, through the structure described above, the retreating distance of the cannula 21 is easily controlled with one hand by repeatedly pressing the first handle 51 so that a small or large amount of sampling may be easily controlled.

Referring to FIGS. 5 and 15, a checking window 122 is formed open in a portion of the housing 10, and a marking portion 43 is formed in a region of an outer surface of the hub block 40, the region corresponding to the checking window 122 in each of the first and second loading states, to allow a loading count to be checked.

In particular, referring to FIG. 15, as loading is repeated through the functional execution described above, a loading state such as "0", "1", or "2" may be exposed through the checking window 122 such that a practitioner may check the loading state.

Referring to FIGS. 5, 9, 10, and 13, the master block 30 includes a connecting bar 33, to which the cannula 21 is fixed. The connecting bar 33 moves together with the cannula 21 in the first or second direction D1 or D2 along a sliding space 333, which is formed in the master block 30 to guide a moving direction of the connecting bar 33 sliding in the sliding space 333.

For the movement described above, a second handle 331 is formed extending from the connecting bar 33 to protrude outside the housing 10 through a third opening 121, which is formed in a portion of the housing 10 to guide the movement of the connecting bar 33, thereby allowing a moving force to be applied to the connecting bar 33.

In addition, a connecting bar locking device 332 is formed between the second handle 331 and the connecting bar 33. As shown in FIG. 9, the movement of the connecting bar 33 is inhibited by a narrowest opening portion 334 of an opening in a side of the sliding space 333 in a default state. When the second handle 331 is pressed, the connecting bar locking device 332 matches the narrowest opening portion 334, and accordingly, the connecting bar 33 may move in the second direction D2 or the first direction D1 through the narrowest opening portion 334. Accordingly, the movement of the connecting bar 33 with respect to the master block 30 is controlled via the operation of the second handle 331. When the second handle 331 is pulled back while being pressed, the connecting bar 33 is unlocked and pulled back. When the second handle 331 is pushed forward, the connecting bar 33 advances and is then caught in the narrowest opening portion 334 due to the elasticity thereof and maintained in a locked state. For this operation, at least one component selected from the connecting bar 33, the second handle 331, and the connecting bar locking device 332 may include a material that has an elastic force in a pressing direction.

FIG. 14 illustrates the sequence of the operations of the cutting biopsy instrument having the structure described above, according to an embodiment.

A stage S1 is a ready state. In a stage S2 right before loading, the first handle 51 is separated from the housing 10, and the connector 52 is caught in the sawtooth 441 or 442. Thereafter, as a stage S3 is entered, a pressing force is applied to the first handle 51, and according to a hinge moving mechanism, the connector 52 applies a force to the sawtooth 441 or 442 in the second direction D2 such that the hub block 40 is moved in the second direction D2 by a predetermined distance "a". As a result, the loading is completed. At this time, since the movement of the master block 30 is inhibited by the first holding unit 13, the master block 30 is separated from the hub block 40 by the predetermined distance "a", and the first spring 50 is stretched, and therefore, a restoring force is generated in the first spring 50. At this time, the second spring 60 is compressed.

In one stage of the stages S1 through S3, a user may simultaneously insert the cannula 21 and the stylet 20 of the cutting biopsy instrument into the tissue of a patient and be ready for shooting.

Thereafter, when a pressing force P1 and/or a pressing force P2 is applied to the first shooting unit 181 and/or the second shooting unit 191, a first shooting stage S4 commences. In other words, when the pressing force P1 and/or the pressing force P2 is applied to the first shooting unit 181 and/or the second shooting unit 191, the first fixing unit 31 is pressed, and the master block 30 is disengaged from the first holding unit 13 according to the mechanism described above. Accordingly, the master block 30 is moved by the restoring force of the first spring 50 in the second direction D2 by a predetermined distance "b".

When the first shooting stage S4 is completed, a second shooting stage S5 commences. In other words, as the master block 30 is moved in the second direction D2, the releasing unit 32 applies a pressing force to the second fixing unit 42, thereby disengaging the hub block 40 from the second holding unit 14. As a result, the hub block 40 moves in the first direction D1 by a predetermined distance "c" while pushing the master block 30 in the first direction D1, and accordingly, the cannula 21 moves in the first direction D1 and cuts the tissue such that a cut portion of the tissue is hermetically accommodated in the tissue sampling groove 202 of the stylet 20.

Accordingly, when the stylet 20 is shooted forward, the stylet is prevented from not penetrating dense epithelium tissue or hard calcified tissue or from being bent. Therefore, difficulties occurring in a procedure because a tuber is pushed back or the stylet does not reach an exact area of sampling target tissue may be removed.

The predetermined distances "a", "b", and "c" may be identical. However, the predetermined distances "a", "b", and "c" may be construed as being different from one another due to a slight error occurring when the functions of embodiments are carried out.

Thereafter, as described above, a tissue collecting stage S6 commences. In other words, the connecting bar 33 is moved in the master block 30 according to the operating mechanism described above, without moving the master block 30 and the hub block 40, such that the cannula 21 is retreated in the second direction D2. As a result, the tissue sampling groove 202 is exposed such that the tissue may be collected. Thereafter, the stage S1 may be repeated to enable repetitive sampling.

Figure 19:
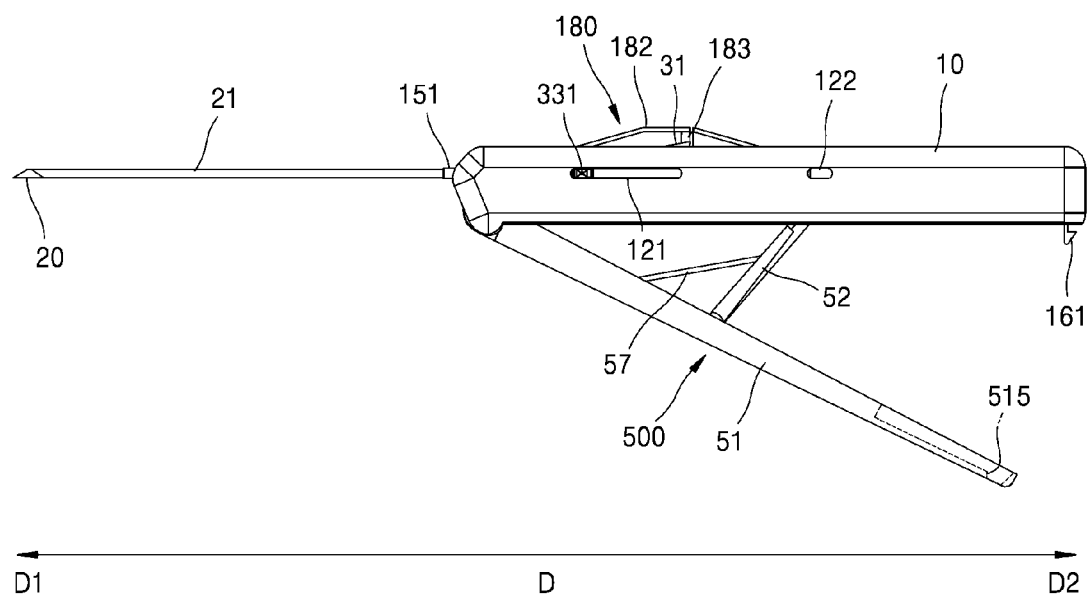
FIG. 19 is a diagram of a cutting biopsy instrument according to an embodiment of the present disclosure.
Figure 20:
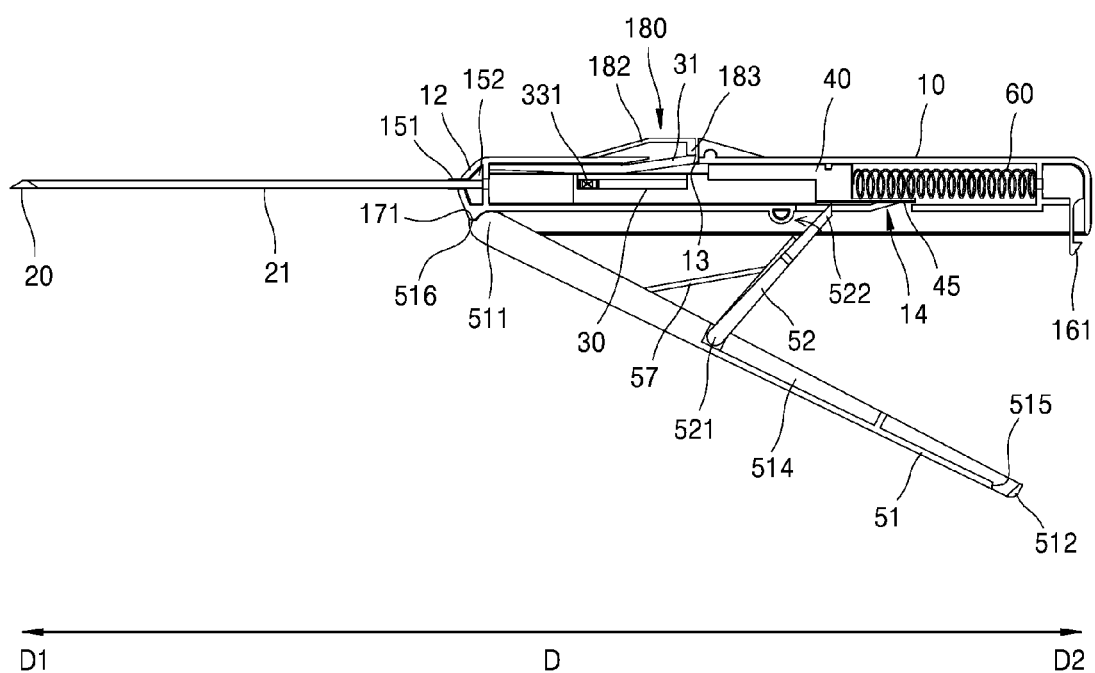
FIG. 20 is a partial cross-sectional view of the cutting biopsy instrument of FIG. 19.

FIG. 19 is a side view of a cutting biopsy instrument according to an embodiment of the present disclosure, and FIG. 20 is a partial cross-sectional view of the cutting biopsy instrument of FIG. 19.

Referring to FIGS. 19 and 20, the cutting biopsy instrument may include the housing 10, the needle set 200, the master block 30, the hub block 40, the first spring 50, the second spring 60, the loading unit 500, and the shooting unit 180.

Figure 21:
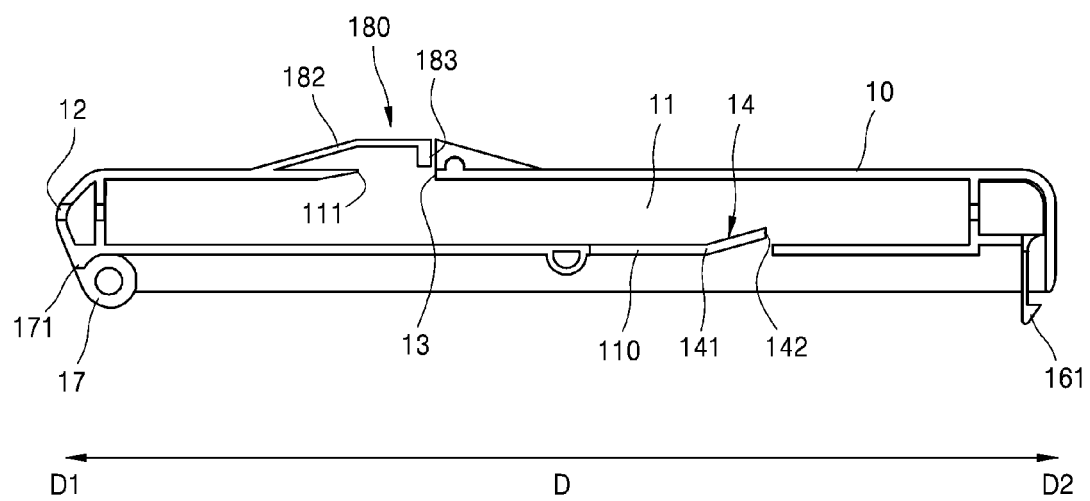
FIG. 21 is a cross-sectional view of a housing of a cutting biopsy instrument, according to an embodiment of the present disclosure.

As shown in FIG. 21, the housing 10 may extend along the axis direction D and include the hollow portion 11, which extends inside the housing 10 in a length direction of the housing 10. The hollow portion 11 may make an airtight space. The housing 10 may have a first opening 110 communicating with the hollow portion 11 and may connect the hub block 40 to the loading unit 500 via the first opening 110, as described below.

The hole 12 is formed in an end of the housing 10. The hole 12 may communicate with the hollow portion 11. As described below, the needle set 200 may pass through the hole 12.

The housing 10 may include a second opening 111, which may be arranged opposite the first opening 110 and may communicate with the hollow portion 11.

The shooting unit 180 may be arranged on a top of the housing 10.

The shooting unit 180 may be adjacent to the second opening 111 and may include a first shooting unit 182 and a second shooting unit 183. The first shooting unit 182 may have elasticity in a direction roughly perpendicular to the axis direction D, i.e., in a vertical direction in the drawings, and may extend separated from the second opening 111. The second shooting unit 183 may extend from an end of the first shooting unit 182 toward the second opening 111 and may be provided to selectively enter the second opening 111 according to a user's pressing operation on the shooting unit 180.

The shooting unit 180 may be integrally formed with the housing 10. In particular, an end of the first shooting unit 182 may be connected to the housing 10. When the shooting unit 180 is integrally formed with the housing 10, the number of components may be reduced and assembly of the shooting unit 180 and the housing 10 may be skipped, and therefore, mass productivity may be enhanced.

The hinge portion 17 is arranged at an end of the housing 10 to be adjacent to the hole 12. The hinge portion 17 may be arranged away from the shooting unit 180 with the hollow portion 11 therebetween. The first handle 51 of the loading unit 500, which will be described below, may be hinged to the hinge portion 17. According to embodiments illustrated in the drawings, the hinge portion 17 is in an end portion of the housing 10 in the first direction D1, but the present disclosure is not limited thereto. The hinge portion 17 may be arranged in an end portion of the housing 10 in the second direction D2. In this case, a locking unit 161, which will be described below, may be arranged in the end portion of the housing 10 in the first direction D1.

According to an embodiment illustrated in FIG. 20, a support block 152 may be further arranged at the end of the housing 10 to be adjacent to the hole 12. The support block 152 has an interior communicating with the hole 12. A support guide 151 may extend in the first direction D1 passing through the hole 12. The support guide 151 may have a pipe shape coaxial with the hole 12 and thus communicate with the hole 12.

The needle set 200, which will be described below, may be provided to penetrate the support block 152. Accordingly, at least the support guide 151 of the support block 152 may have an inner diameter corresponding to an outer diameter of the needle set 200. The support block 152 may minimize the sway of the needle set 200 during a procedure, thereby helping exact target sampling. In addition, different sizes of the needle set 200 are used according to target tissue and the type of procedures. According to the embodiment, the support block 152 is configured to have a size corresponding to the needle set 200, and particularly, the inner diameter of the support guide 151 corresponds to the outer diameter of the needle set 200, and therefore, the needle set 200 may be changed by simply changing the support block 152.

The housing 10 may further include a first stopper 171. The first stopper 171 may be arranged between the hole 12 and the hinge portion 17 and closer to the hinge portion 17. The first stopper 171 and/or a second stopper 516, which will be described below, may limit a rotation angle of the first handle 51 to a certain range.

The loading unit 500 may include the first handle 51 and the connector 52. The end 511 of the first handle 51 may be hinged to the hinge portion 17 of the housing 10, and the opposite end 512 of the first handle 51 may be open. The first handle 51 may include the second stopper 516 adjacent to the first stopper 171. The second stopper 516 may come into contact with the first stopper 171 when the first handle 51 rotates around the hinge portion 17 to a maximum angle such that the first handle 51 may be inhibited from further rotating around the hinge portion 17. Although both the first stopper 171 and the second stopper 516 are provided in the current embodiment, the present disclosure is not limited thereto. At least one selected from the first stopper 171 and the second stopper 516 may be sufficient.

The end 521 of the connector 52 is rotatably hinged to a roughly central portion of the first handle 51, and the opposite end 522 of the connector 52 faces the hub block 40. An elastic member 57 may be connected between the connector 52 and the first handle 51, and accordingly, the opposite end 522 of the connector 52 may receive an elastic force in the first direction D1. The first handle 51 may include a groove 514 in a portion of the first handle 51, with which the connector 52 is combined via rotation. Accordingly, the connector 52 may be positioned in the groove 514 when the first handle 51 comes to the vicinity of the housing via rotation and prevented from interfering with the motion of the first handle 51.

The locking unit 161 may be arranged in an opposite end of the housing 10, i.e., an end opposite the hinge portion 17. The locking unit 161 extends in the direction perpendicular to the axis D. Referring to FIG. 20, an end portion of the locking unit 161 has a hook shape such that the locking unit 161 may be hooked up to the opposite end 512 of the first handle 51 through a hole 515 in the opposite end 512. The locking unit 161 may have elasticity in a direction perpendicular to a length direction thereof and, as described below, may release the fixation of the first handle 51 via a user's simple operation. The locking unit 161 may not be necessarily joined to the housing 10 but may be joined to the opposite end 512 of the first handle 51. In this case, the hole 515 may be formed in the housing 10.

Figure 22:
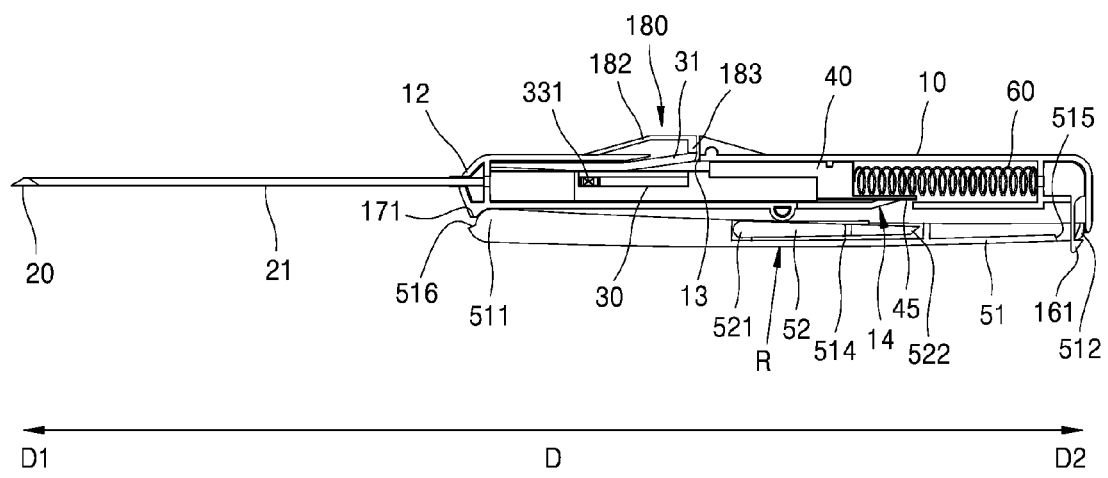
FIG. 22 is a diagram of a cutting biopsy instrument according to another embodiment of the present disclosure.

As shown in FIG. 22, the first handle 51 may have a certain curvature in a length direction thereof in a state where the first handle 51 is fastened to the housing 10 via the locking unit 161. The first handle 51 may include a metal material and/or a synthetic resin material and may itself have a certain elasticity. Accordingly, in the state where the first handle 51 is fastened to the housing 10 via the locking unit 161, the first handle 51 may have an elastic force in a direction roughly perpendicular to the length direction thereof, e.g., in a direction opposite the locking unit 161. When the first handle 51 has the elastic force in the direction perpendicular to the length direction thereof, the first handle 51 has a potential in a direction in which the fastening via the locking unit 161 is released, and accordingly, the fastening of the first handle 51 via the locking unit 161 may be released at a user's light touch of the locking unit 161, which has a hook shape. This may enhance handleability of the first handle 51 for users.

The housing 10 may include the first holding unit 13 and the second holding unit 14.

The first holding unit 13 may selectively engage with the master block 30 and thus provide the master block 30 with resistance against the first elastic force of the first spring 50. According to an embodiment, the first holding unit 13 may be implemented by an end portion of the second opening 111 in the second direction D2 in the housing 10. The second shooting unit 183 may be arranged adjacent to the first holding unit 13 and may disengage the master block 30 from the first holding unit 13 by pressing a portion of the master block 30 caught in the first holding unit 13.

The second holding unit 14 may selectively engage with the hub block 40 and thus provide the hub block 40 with resistance against the second elastic force of the second spring 60. According to an embodiment, the second holding unit 14 may be implemented by an elastic supporting body, which extends from the first opening 110 of the housing 10 in the second direction D2. An end 141 of the second holding unit 14 is connected to the housing 10, and an opposite end 142 of the second holding unit 14 extends from the end 141 to slant toward the hollow portion 11. The opposite end 142 of the second holding unit 14 may be separated from the housing 10 to perform an elastic motion around the end 141 to a certain degree. Therefore, as described below, the master block 30 moves toward the hub block 40 according to a user's shooting operation and thus presses the second holding unit 14 such that the selective engagement between the hub block 40 and the second holding unit 14 may be released.

As shown in FIG. 19, the housing 10 may further include the third opening 121. The third opening 121 may be formed in a side of the housing 10. For example, the third opening 121 may be formed in a lateral surface of the housing 10 to be adjacent to the shooting unit 180, as shown in FIG. 19. As described below, the second handle 331 may be exposed outside the housing 10 through the third opening 121 such that a user may operate the second handle 331.

Similarly to the embodiments described above, the needle set 200 may include the stylet 20 and the cannula 21.

At least the cannula 21 of the needle set 200 may be coupled to the master block 30. The master block 30 is arranged in the hollow portion 11. The stylet 20 may be provided to penetrate the master block 30.

Figure 23:
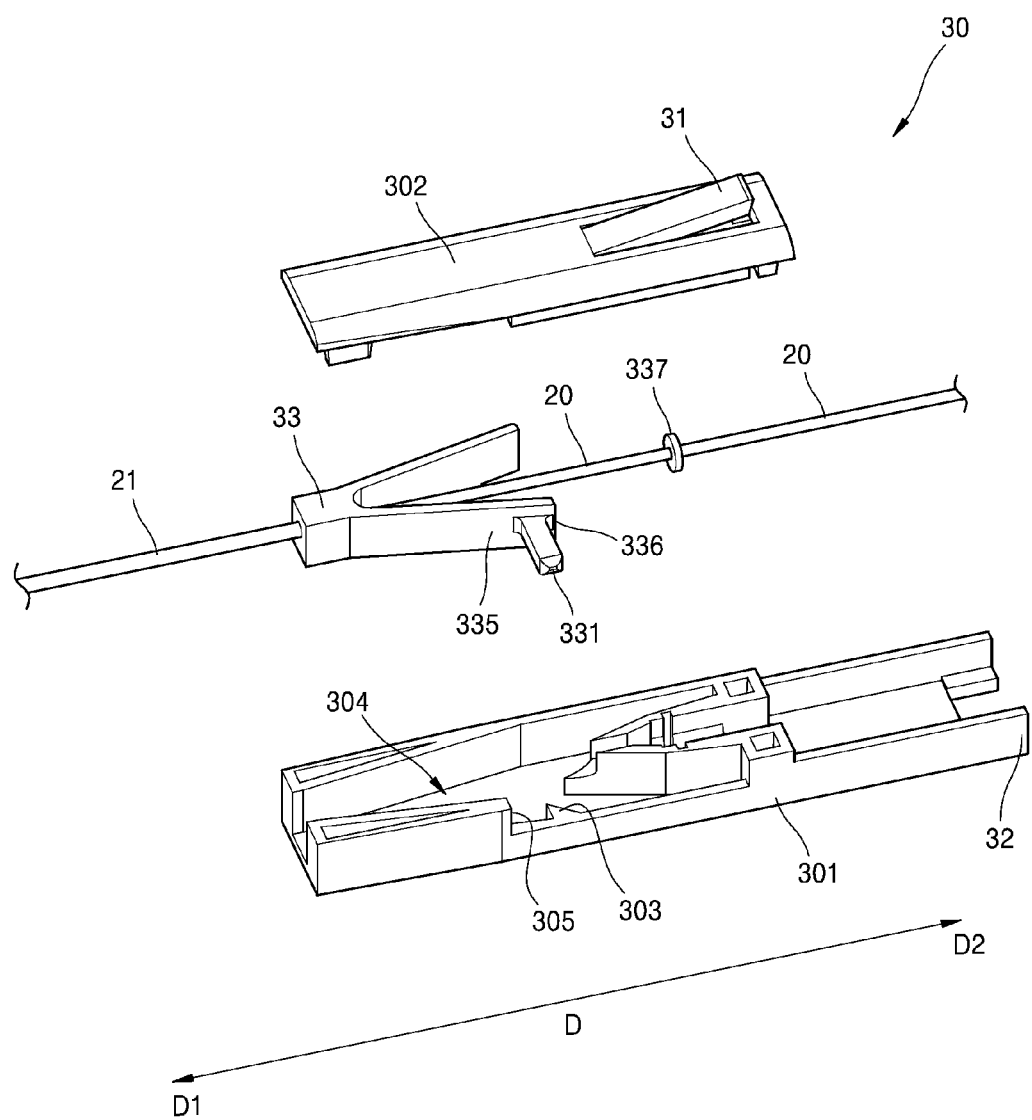
FIG. 23 is an exploded view of a master block of a cutting biopsy instrument, according to an embodiment of the present disclosure.

Referring to FIG. 23, the master block 30 may include a base 301 and a cover 302. The base 301 has a space 304 such that the connecting bar 33 may be coupled to the base 301. An opening 305 is formed in a side of the base 301 such that the second handle 331 of the connecting bar 33 may be exposed. The base 301 may include a third holding unit 303 adjacent to the opening 305. The third holding unit 303 may have a wedge shape protruding from a side wall of the base 301 at the bottom toward the space 304 and thus selectively inhibit the motion of the connecting bar 33. However, the third holding unit 303 is not limited thereto and may have a protruding shape projecting toward the space 304. For example, the third holding unit 303 may have any shape as long as the third holding unit 303 selectively inhibits the motion of the connecting bar 33.

The connecting bar 33 may be fixedly coupled to an end of the cannula 21 and may be provided such that the stylet 20 may penetrate the connecting bar 33.

The connecting bar 33 may be embedded in the master block 30. The connecting bar 33 may be mounted inside the master block 30 and provided to be movable in a length direction of the master block 30. The connecting bar 33 may include an elastic portion 335 in a remaining portion other than a portion coupled to the cannula 21. The elastic portion 335 has a certain elasticity in a direction perpendicular to the length direction of the master block 30. The second handle 331 may be provided adjacent to an end 336 of the elastic portion 335 to be exposed outside the master block 30. The second handle 331 may be exposed outside the master block 30 via the opening 305 and exposed outside the housing 10 via the third opening 121 formed in the housing 10, as shown in FIG. 19. The position of the elastic portion 335 of the connecting bar 33 may be selectively fixed by the third holding unit 303. In other words, when the connecting bar 33 is positioned at an end of the master block 30, an end 336 of the elastic portion 335 may be caught in the third holding unit 303. When the elastic portion 335 is bent by an external pressure in a direction perpendicular to the length direction of the master block 30, the end 336 may be disengaged from the third holding unit 303.

When a user operates the second handle 331, the user may move the connecting bar 33 by pressing the second handle 331 in a direction perpendicular to the length direction of the master block 30 and moving the second handle 331 in the length direction of the master block 30 along the third opening 121. As the connecting bar 33 is moved as described above, the cannula 21 coupled to the connecting bar 33 may be moved in the same manner, and accordingly, the tissue sampling groove 202 of the stylet 20 may be exposed, as shown in FIG. 6.

A fixing block 337 may be further provided adjacent to the connecting bar 33 such that the stylet 20 penetrates the fixing block 337. The fixing block 337 may be fixedly coupled to the inside of the master block 30. The first spring 50 may be fixed to the fixing block 337, as described below.

The cover 302 is combined with the base 301. The first fixing unit 31 may be provided on a surface of the cover 302 to be elastically movable in a direction perpendicular to the length direction of the master block 30. The first fixing unit 31 may protrude from the surface of the cover 302 and move with elasticity in an opposite direction to the protruding direction. Referring to FIG. 21, the first fixing unit 31 may be caught in the first holding unit 13, and accordingly, the motion of the master block 30 may be restrained by the first holding unit 13. The first shooting unit 182 of the shooting unit 180 presses the first fixing unit 31 according to a user's operation, and accordingly, the first fixing unit 31 may be released from the first holding unit 13.

The master block 30 may further include the releasing unit 32. The releasing unit 32 may be arranged in a portion of the master block 30, wherein the portion faces the hub block 40. According to an embodiment, the releasing unit 32 may extend toward the hub block 40. According to an embodiment, the releasing unit 32 may be a plate-shape member extending toward the hub block 40.

The hub block 40 may be arranged in the hollow portion 11. The stylet 20 may penetrate the hub block 40. The hub block 40 may be aligned with master block 30 along the axis direction D. Referring to FIG. 20, the hub block 40 may be adjacent to the master block 30.

Figure 24:
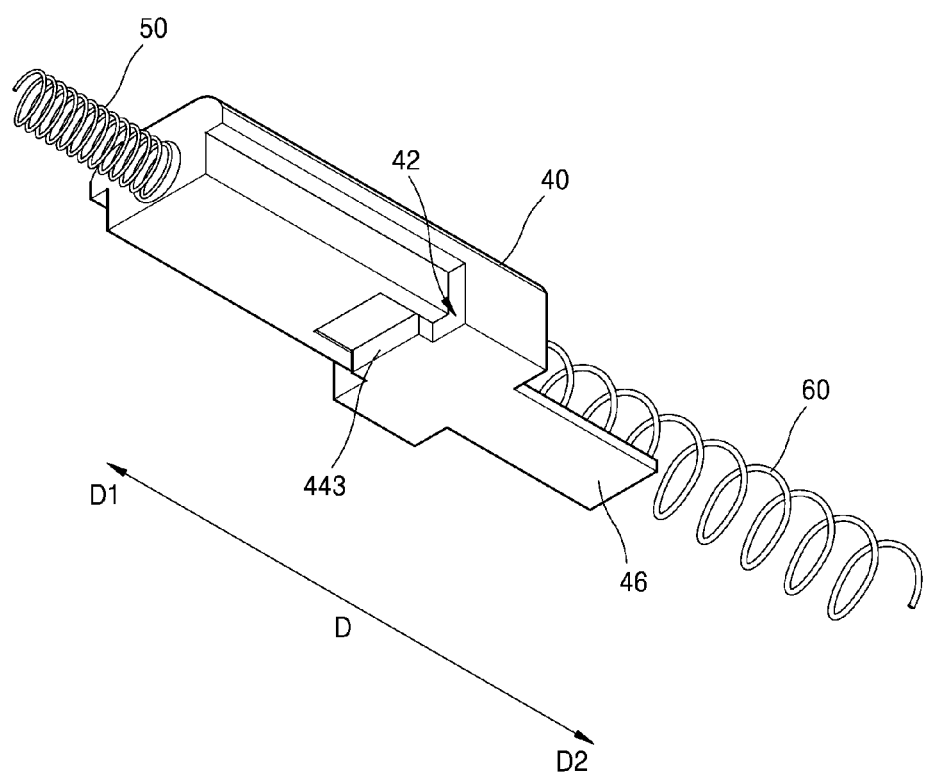
FIG. 24 is a diagram of a hub block of a cutting biopsy instrument, according to an embodiment of the present disclosure.

Referring to FIG. 24, according to an embodiment, the first spring 50 may be coupled to an end of the hub block 40 and the second spring 60 may be coupled to an opposite end of the hub block 40.

The hub block 40 may include a fourth holding unit 443. The fourth holding unit 443 may be formed toward the loading unit 500. According to an embodiment illustrated in FIG. 24, the fourth holding unit 443 may be implemented as a step on a bottom surface of the hub block 40. Referring to FIG. 20, the fourth holding unit 443 is provided to hold the opposite end 522 of the connector 52. Accordingly, when a user presses the first handle 51 toward the housing 10 with one hand, the hub block 40 moves in the second direction D2 with the connector 52 being held by the fourth holding unit 443.

The hub block 40 may include the second fixing unit 42. The second fixing unit 42 may be a step formed in the hub block 40 in a direction perpendicular to the axis D. When the hub block 40 moves in the second direction D2, the hub block 40 may be fixed to the second holding unit 14 via the second fixing unit 42. According to an embodiment, the second fixing unit 42 and the releasing unit 32 of the master block 30 may have corresponding shapes such that the second fixing unit 42 may engage with the releasing unit 32. When the hub block 40 moves in the second direction D2 over the second holding unit 14, the opposite end 142 of the second holding unit 14 comes into contact with the second fixing unit 42 and fixes the hub block 40, wherein the opposite end 142 is not fixed to the housing 10. In this state, when the master block 30 is moved toward the hub block 40 by the first spring 50, the releasing unit 32 of the master block 30 engages with the second fixing unit 42 and presses the opposite end 142 of the second holding unit 14, and accordingly, the second fixing unit 42 is released from the hold of the opposite end 142. In this case, the master block 30 and the hub block 40 are moved in the first direction D1 by the second spring 60.

The hub block 40 may further include an extension unit 46, which extends from a portion coupled to the second spring 60 toward the second spring 60. The extension unit 46 may block the first opening 110 in at least one state, e.g., an unloaded state, such that the hollow portion 11 may be hermetically sealed. Since the hollow portion 11 is roughly maintained hermetically sealed, when the master block 30 retreats in the second direction D2 during shooting, the volume of space generated by the movement of the master block 30 changes, and accordingly, negative pressure may be created in a space between the cannula 21 and the stylet 20 and in the tissue sampling groove 202. Tissue may be well received in the tissue sampling groove 202 due to the negative pressure, and accordingly, the tissue may be prevented from being pushed and effectively cut during cutting of the tissue.

The first spring 50 and the second spring 60 may be aligned with the master block 30 and the hub block 40 along the axis direction D in the hollow portion 11.

According to an embodiment, the first spring 50 may be aligned with the master block 30 and the hub block 40 along the axis direction D in the hollow portion 11. The second spring 60 may be aligned with the master block 30, the hub block 40, and the first spring 50 along the axis direction D in the hollow portion 11.

At this time, the first spring 50 may provide the master block 30 with a first elastic force in the first direction D1 parallel with the axis direction D, and the second spring 60 may provide the hub block 40 with a second elastic force in a direction parallel with the axis direction D.

Figure 25:
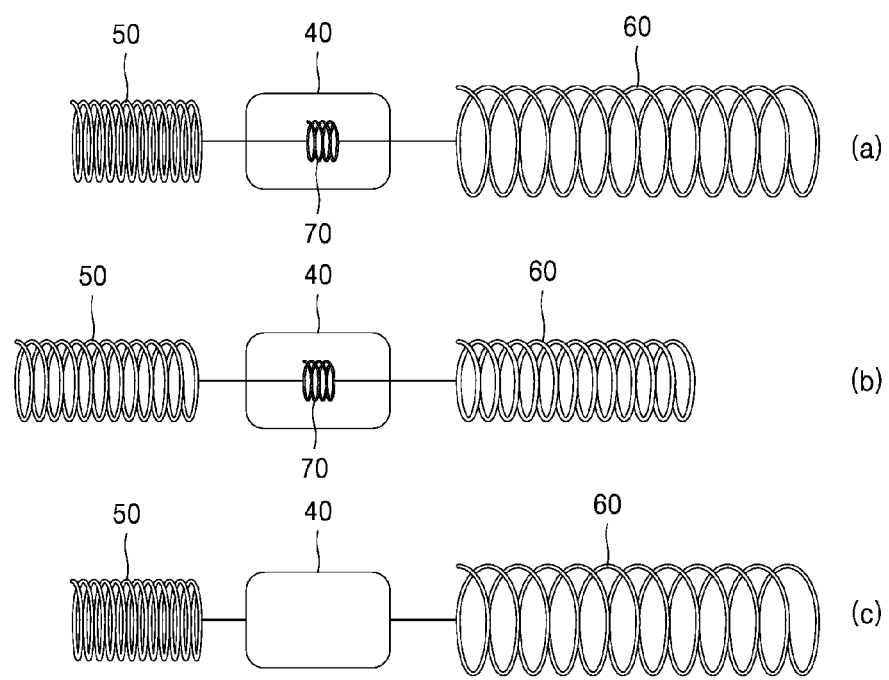
FIGS. 25(a) through 25(c) are diagrams of the combined state of first and second springs and a hub block, according to different embodiments of the present disclosure.

The combined structure of the hub block 40, the first spring 50, and the second spring 60 may vary. In other words, when the first spring 50 and the second spring 60 are combined with the hub block 40, of which the position may be selectively fixed, in different directions with the hub block 40 between the first spring 50 and the second spring 60, the first spring 50 having an extension pitch, the second spring 60 having a compression pitch, and a connector 70 connecting the first spring 50 to the second spring 60 may be formed by changing the winding pitch and/or radius of a single spring, and the hub block 40 may be formed to surround the connector 70, as shown in FIG. 25(a). According to an embodiment, as shown in FIG. 25(b), the first spring 50 having a weak compression pitch, the second spring 60 having a strong compression pitch, and the connector 70 connecting the first spring 50 to the second spring 60 may be formed by changing the winding pitch and/or radius of a single spring, and the hub block 40 may be formed to surround the connector 70. According to an embodiment, as shown in FIG. 25C, the first spring 50 and the second spring 60 may be individually formed and may be respectively coupled to opposite ends of the hub block 40.

According to the structure of the first spring 50 and the second spring 60, the hub block 40 may construct various kinds of drive mechanisms in addition to the embodiments described above and may thus be used as a drive unit for various machines requiring continuous operation in opposite directions. In addition, a compound spring having different winding pitches and/or radii is used, and therefore, the number of components may be reduced and a machine structure may be simplified.

Referring to FIG. 19, the checking window 122 is formed open in a portion of the housing 10, and a marking is formed in a region of an outer surface of the hub block 40, wherein the region corresponds to the checking window 122. Accordingly, a user may identify a loaded state or an unloaded state by checking the marking through the checking window 122.

Figure 26:
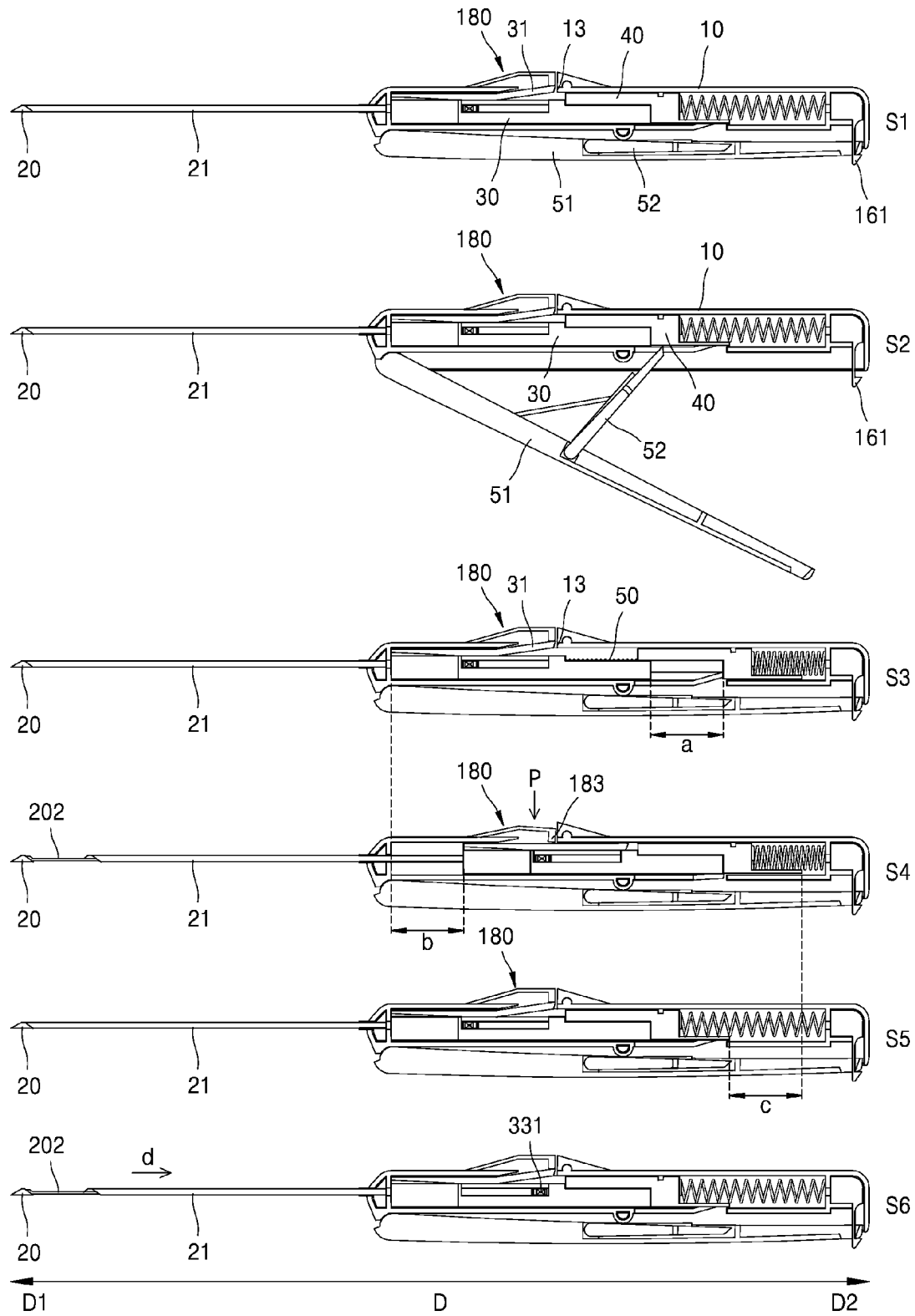
FIG. 26 is a diagram for explaining the operating stages of a cutting biopsy instrument, according to an embodiment of the present disclosure.

FIG. 26 shows the flow of operations of a cutting biopsy instrument having the structure described above, according to an embodiment of the present disclosure.

The stage S1 is a ready state. At this time, the locking unit 161 of the first handle 51 may be locked to the hole 515, and the opposite end 522 of the connector 52 may not be held by the fourth holding unit 443. In this state, the first handle 51 has a certain elastic force in a lock releasing direction, and therefore, the lock of the first handle 51 may be simply released by a user's light touch on an end of the locking unit 161 in the locking releasing direction, e.g., the first direction D1, wherein the end of the locking unit 161 is exposed outside the hole 515. When the lock is released, the first handle 51 automatically enters the stage S2 right before loading since the rotation angle of the first handle 51 is restrained by the first stopper 171 and/or the second stopper 516. In this position, the opposite end 522 of the connector 52 may be automatically moved to a position at which the opposite end 522 is held by the fourth holding unit 443.

The stage S2 is a state right before loading. In the stage S2, the first handle 51 is separated from the housing 10 and the opposite end 522 of the connector 52 is held by the fourth holding unit 443.

The stage S3 is a loaded state. In the stage S3, when a user applies a pressing force to the first handle 51, the connector 52 applies a force to the fourth holding unit 443 in the second direction D2 according to the hinge moving mechanism, and accordingly, the hub block 40 is moved in the second direction D2 by the predetermined distance "a". As a result, the loading is completed. At this time, the second fixing unit 42 of the hub block 40 may be fixed to the second holding unit 14 such that the position of the hub block 40 may be fixed.

Such a loading operation is carried out by a user grasping the cutting biopsy instrument and pressing the first handle 51 toward the housing 10 with one hand. Accordingly, the user may easily finish the loading operation only with power pressing the first handle 51 while keeping the other hand free.

At this time, since the master block 30 is suppressed from moving by the first holding unit 13, the master block 30 is separated from the hub block 40 by the predetermined distance "a", and the first spring 50 is stretched, and accordingly, a first elastic force is generated in the first spring 50. At this time, the second spring 60 is compressed and thus has a second elastic force.

In one of the stages 51 through S3, the user may simultaneously insert the cannula 21 and the stylet 20 of the cutting biopsy instrument into the tissue of a patient and be ready for shooting.

Thereafter, when a pressing force P is applied to the first shooting unit 181, the first shooting stage S4 commences. In other words, when the pressing force P is applied to the first shooting unit 181, the first shooting unit 182 presses the first fixing unit 31, and accordingly, the first fixing unit 31 may be released from the first holding unit 13. Accordingly, the master block 30 is moved by the restoring force of the first spring 50 in the second direction D2 by the predetermined distance "b", and simultaneously, the cannula 21 fixed to the master block 30 moves in the second direction D2 by the distance "b", thereby exposing the tissue sampling groove 202. At this time, tissue to be sampled may be pushed and received in the tissue sampling groove 202.

When the first shooting stage S4 is completed, the second shooting stage S5 commences. In other words, as the master block 30 is moved in the second direction D2, the releasing unit 32 of the master block 30 engages with the second fixing unit 42 and presses the opposite end 142 of the second holding unit 14, and accordingly, the second fixing unit 42 is released from the hold of the opposite end 142. In this case, the master block 30 and the hub block 40 are moved in the first direction D1 by the second spring 60, and simultaneously the cannula 21 fixed to the master block 30 moves in the first direction D1, thereby covering the tissue sampling groove 202 and cutting an upper portion of the tissue received in the tissue sampling groove 202 such that the tissue is hermetically accommodated in the tissue sampling groove 202 in the stage S5.

The predetermined distances "a", "b", and "c" may be identical. However, the predetermined distances "a", "b", and "c" may be construed as being different from one another due to a slight error occurring when the functions of embodiments are carried out.

Thereafter, as described above, the tissue collecting stage S6 may commence. In other words, the user may release the second handle 331 of the connecting bar 33 from the third holding unit 303 by pressing the second handle 331 and move the second handle 331 in the second direction D2, thereby moving the cannula 21 in the second direction D2. As a result, the tissue sampling groove 202 of the stylet 20 is exposed such that the tissue may be collected.

It is apparent that combinations of the embodiments described above may be implemented. In other words, features of one of the embodiments may also be applied to other embodiments.

According to the embodiments, sampled tissue may be collected via a simple operation as described above. Accordingly, a user may collect tissue with only one hand grasping a cutting biopsy instrument and thus keep the other hand free. Therefore, the user may immediately proceed to another tissue sampling operation, and accordingly, consecutive samplings may be easily carried out.

As described above, a user may perform the loading, shooting, and collecting operations with only one hand grasping a cutting biopsy instrument while positioning an ultrasonic instrument at a target with the other hand, thereby easily executing a whole procedure.

While embodiments have been described with reference to particular embodiments and drawings, various changes and modifications may be made in the above descriptions by those of ordinary skill in the art. For example, even when the techniques described above are performed in a different order than described above, and/or the components such as systems, structure, devices, circuits, etc. described above are coupled to or combined with each other in different manners than described above or substituted or replaced with other components or equivalents, proper results may be obtained. Therefore, other implements, other embodiments, and equivalents to the scope of the claims are included in the scope of the claims described below.

INDUSTRIAL APPLICABILITY

A cutting biopsy instrument may be used as an instrument for sampling biological tissue in a living body.

The invention claimed is:
1. A cutting biopsy instrument comprising:
a housing extending in an axis direction and including a hollow portion extending in a length direction of the housing and at least one opening communicating with the hollow portion;
a needle set including a stylet and a cannula and being partially arranged in the hollow portion, the stylet having a tissue sampling groove at an end, and the cannula having a pipe shape to receive the stylet therein and being shorter than the stylet;
a master block connected to an end of the cannula, penetrated by the stylet, and arranged in the hollow portion;
a hub block penetrated by the stylet, arranged in the hollow portion, and aligned with the master block in the axis direction;
a first spring arranged in the hollow portion, aligned with the master block and the hub block in the axis direction, and providing the master block with a first elastic force in a direction parallel with the axis direction;
a second spring arranged in the hollow portion, aligned with the master block, the hub block, and the first spring in the axis direction, and providing the hub block with a second elastic force in the direction parallel with the axis direction;
a first holding unit arranged in the housing and provided to selectively engage with the master block to provide resistance against the first elastic force to the master block;
a second holding unit arranged in the housing and provided to selectively engage with the hub block to provide resistance against the second elastic force to the hub block;
a loading unit including a first handle provided to be coupled to the housing to apply a force to the hub block in the axis direction and a connector coupled to the first handle, the connector being caught in the hub block to move the hub block in a loading procedure; and
a shooting unit arranged at the housing and provided to selectively disengage the master block from at least the first holding unit,
wherein the hub block is not coupled to the needle set,
wherein the stylet is fixed within the housing so as not to move in the axis direction,
wherein the first holding unit provides the master block with the resistance against the first elastic force after the loading procedure by the loading unit, and
wherein the second holding unit provides the hub block with the resistance against the second elastic force after the loading procedure by the loading unit.
2. The cutting biopsy instrument of claim 1, further comprising
a locking unit arranged between an end of the first handle and the housing and provided to selectively fasten the end of the first handle to the housing,
wherein the first handle has an elastic force in a direction opposite the locking unit.
3. The cutting biopsy instrument of claim 1, further comprising
a stopper arranged at at least one portion selected from an end of the first handle and a portion of the housing adjacent to the first handle and provided to restrain a rotation angle of the first handle.
4. The cutting biopsy instrument of claim 1, further comprising an extension unit extending from the hub block toward the second spring and provided to block the at least one opening of the housing in at least one state.

5. The cutting biopsy instrument of claim 1, further comprising
a connecting bar embedded in the master block, provided to move in a length direction of the master block, coupled to the end of the cannula, and including a second handle exposed outside the master block,
wherein the master block includes a third holding unit selectively inhibiting a motion of the connecting bar.

6. The cutting biopsy instrument of claim 1, wherein
the master block includes a releasing unit extending toward the hub block and provided to release the resistance of the second holding unit.

* * * * *